(12) United States Patent
Toriyama et al.

(10) Patent No.: US 8,066,409 B2
(45) Date of Patent: Nov. 29, 2011

(54) LIGHT SOURCE DEVICE

(75) Inventors: Seiki Toriyama, Hino (JP); Mutsumi Oshima, Hachioji (JP); Shinji Yamashita, Tachikawa (JP); Keiichi Tsuchida, Fuchu (JP); Tomoya Takahashi, Hachioji (JP); Atsushi Shimada, Hachioji (JP); Yusuke Yabe, Hachioji (JP); Kyosuke Mizuno, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 243 days.

(21) Appl. No.: 12/188,779

(22) Filed: Aug. 8, 2008

(65) Prior Publication Data
US 2009/0052185 A1   Feb. 26, 2009

(30) Foreign Application Priority Data

Aug. 23, 2007 (JP) ................. 2007-217489

(51) Int. Cl.
*F21V 9/00* (2006.01)
*F21S 8/00* (2006.01)

(52) U.S. Cl. ........................................ 362/293; 362/268
(58) Field of Classification Search ............. 362/293, 362/268, 574; 359/811, 818, 819, 821, 827
See application file for complete search history.

(56) References Cited

U.S. PATENT DOCUMENTS

| 2,659,269 | A | * | 11/1953 | Castelli | 351/91 |
| 4,029,956 | A | * | 6/1977 | Leibundgut et al. | 362/268 |
| 4,187,534 | A | * | 2/1980 | Tichenor et al. | 362/268 |
| 5,203,627 | A | * | 4/1993 | Kira | 362/374 |
| 5,943,153 | A | * | 8/1999 | Naiki et al. | 359/210.1 |
| 5,993,037 | A | * | 11/1999 | Tomioka et al. | 362/583 |
| 6,728,048 | B2 | * | 4/2004 | Takase | 359/819 |
| 6,897,432 | B2 | * | 5/2005 | Schmidtke et al. | 250/216 |
| 2003/0184853 | A1 | | 10/2003 | Sasaki | |
| 2006/0155166 | A1 | * | 7/2006 | Takahashi et al. | 600/109 |

FOREIGN PATENT DOCUMENTS

| EP | 0 172 680 A1 | 2/1986 |
| JP | 2005-006974 | 1/2005 |
| WO | WO 99/66830 | 12/1999 |

OTHER PUBLICATIONS

Spindler & Hoyer, "Precision Optic", 1988, Spindler & Hoyer, Federal Republic of Germany, XP002540137, p. W6.

* cited by examiner

*Primary Examiner* — David Crowe
(74) *Attorney, Agent, or Firm* — Scully, Scott, Murphy & Presser, P.C.

(57) ABSTRACT

A light source device includes a light-condensing device that condenses an illumination light that is emitted from a light source lamp. The light-condensing device includes at least one lens, a lens holder in which a lens is fixedly provided, and a lens holding member. The lens holding member is a member for fixing a lens to the lens holder. The lens holding member causes at least one circumferential portion of the lens to protrude to the lens holder side, and causes the optical axis of the lens to match the optical axis of the illumination light.

5 Claims, 19 Drawing Sheets

LIGHT SOURCE DEVICE

CROSS REFERENCE TO RELATED APPLICATION

This application claims benefit of Japanese Application No. 2007-217489 filed on Aug. 23, 2007, the contents of which are incorporated by this reference.

BACKGROUND OF THE INVENTION

1. Field of the Invention

The present invention relates to a light source device that enables special light observation using many kinds of special light such as narrow-band light, fluorescence, and infrared light, in addition to normal light observation by white light.

2. Description of the Related Art

Conventionally, an endoscope is used for observing an alimentary tract such as the esophagus, the stomach, the small intestine or the large intestine, or for observing tracheae such as the lungs by inserting an elongated insertion portion into the body. An endoscope also makes it possible to perform various kinds of examinations or curative treatments by passing a treatment instrument through a treatment instrument channel provided in the insertion portion of the endoscope.

When performing an examination, tissue extraction, treatment or the like using an endoscope, a light source device that supplies an illumination light, a control device such as a video processor that generates video signals from optical images of an examination site that are picked up by the endoscope, and a display device that displays endoscopic images of the examination site and the like are used as peripheral endoscopic devices.

In recent years, when performing diagnosis using an endoscope, in addition to normal light observation by white light in which color images of an observation site are displayed on a display device and observed, special light observation is performed that employs fluorescence, infrared light, narrow-band light (also described as "NBI"), and the like as illumination light.

Special light observation makes it possible to, for example, bring blood vessels on the surface of an alimentary tract into clear view for displaying on a display screen. It is therefore possible to distinguish cancer locations that are difficult to find with normal light observation, or to distinguish the size of a cancer or whether a tumor is cancerous or is in a precancerous state or the like.

There is thus a demand for light source devices that, in addition to white light for performing normal light observation as an illumination light, also provide a plurality of kinds of special observation lights as illumination lights. Examples of special observation lights include fluorescence for performing fluorescence observation, infrared light for performing infrared light observation, and NBI for performing NBI observation.

For example, Japanese Patent Application Laid-Open Publication No. 2005-006974 discloses an endoscope apparatus in which, by means of an operation to switch an observation mode, it is possible to only select an observation mode that is compatible with a connected endoscope, and perform observation in that mode. In this endoscope apparatus, as illustrated in FIG. 1, a lamp 101, a filter turret 103, an illumination light aperture (not shown), a rotary filter 104, a rotary motor 105, and a light-condensing device 106 are provided inside a light source device 100. The filter turret 103 is configured to be capable of switching a plurality of optical filters (not shown) by driving of a motor 102. The transmission wavelength bands of the plurality of optical filters differ for each observation mode. The illumination light aperture limits the irradiation light amount. The rotary filter 104 changes the illumination light into, for example, frame sequential light of red (R), green (G), and blue (B). The rotary motor 105 rotatingly drives the rotary filter 104. The light-condensing device 106 includes a lens 106a. The lens 106a of the light-condensing device 106 condenses the frame sequential light onto an incidence plane 112 of a light guide 111 of an unshown endoscope.

The rotary filter 104 includes filters 107 and 108 on the outer circumference side and inner circumference side, respectively. A forward/rearward movement motor 109 that moves the rotary filter 104 forward/rearward in a perpendicular direction to the illumination light path (hereafter, referred to as "optical path") is provided inside the light source device 100. The rotary filter 104 is thus moved forward/rearward by driving of the motor 109. More specifically, the rotary filter 104 is configured to change between a state in which the rotary filter 104 is moved to a position indicated by the solid line so that the outer circumference side filter 107 is disposed in the optical path and a state in which the rotary filter 104 is moved to a position indicated by the dashed line so that the inner circumference side filter 108 is disposed in the optical path.

According to the light source device 100, by switching the optical filters of the filter turret 103, suitably combining rotary operation of the rotary motor 105 with forward/rearward operation of the forward/rearward movement motor 109, and selectively controlling switching of the filters 107 and 108 provided in the rotary filter 104, it is possible to carry out endoscopic observation which switches among a plurality of observation modes.

However, recently various kinds of special lights that are useful for observation have been developed. There is thus a demand from users for a light source device that enables observation using even more kinds of special light. In a light source device, it is possible to perform observation by various kinds of special light by increasing the number of optical filters. For example, in a light source device 100A shown in FIG. 2, a rotary filter 104A is additionally provided to increase the number of filters. However, by additionally providing the rotary filter 104A in the optical path, the position of the lamp 101 of the light source device 100A is displaced by an amount L1 in comparison to the position of the lamp 101 of the light source device 100 shown in the aforementioned FIG. 1. As a result, a disadvantage arises that the size of the light source device increases.

In a light source device 100B shown in FIG. 3, a rotary filter 104A that is additionally added is disposed facing the rotary filter 104, and the rotary motor 105 is provided on the light-condensing device 106 side. According to this configuration, when the rotary motor 105 is moved to the optical path as indicated by the dashed line, interference occurs between the rotary motor 105 and the light-condensing device 106. Accordingly, a motor relief part 114 as illustrated by a chain double-dashed line is provided in a lens base 113 comprising the light-condensing device 106 as shown in FIG. 4.

In this connection, the dashed line position is a position at which the rotary filter 104A and the rotary motor 105 are separated the most from the optical path. In other words, the rotary filter 104A and the rotary motor 105 advance and retreat to disposition positions indicated by the dashed line and the solid line. According to this configuration, interference between the rotary motor 105 and the light-condensing device 106 is prevented, and the position of the lamp 101 of the light source device 100B and the position of the lamp 101 of the light source device shown in the aforementioned FIG. 3 are substantially the same position. Thus, it is possible to perform observation using many kinds of special lights without making the light source device 100B larger than the light source device 100.

SUMMARY OF THE INVENTION

A light source device of the present invention includes a light-condensing device that condenses an illumination light that is emitted from a light source lamp. The light-condensing device includes at least one lens; a lens holder in which the lens is fixedly provided; and a lens holding member that causes at least one circumferential portion of the lens to protrude to a side of the lens holder, causes an optical axis of the lens to match an optical axis of the illumination light, and fixes the lens in the lens holder.

The above and other objects, features and advantages of the invention will become more clearly understood from the following description referring to the accompanying drawings.

DETAILED DESCRIPTION OF THE PREFERRED EMBODIMENTS

An embodiment of the present invention is described hereafter with reference to the attached drawings.

FIG. 5 to FIG. 22 illustrate one embodiment of the present invention.

Figure 1:
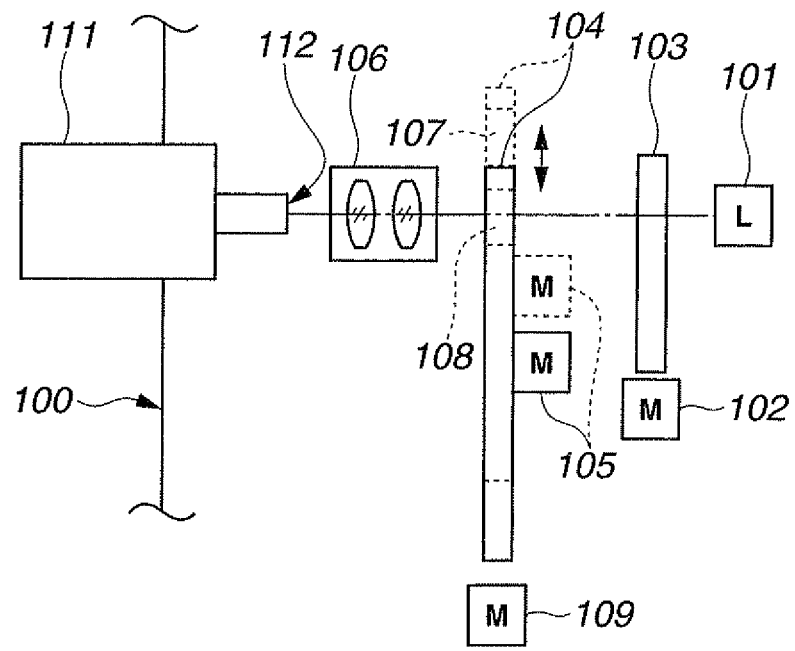
FIG. 1 is an explanatory drawing that describes an abbreviated configuration of an illumination portion of a conventional light source device.
Figure 2:
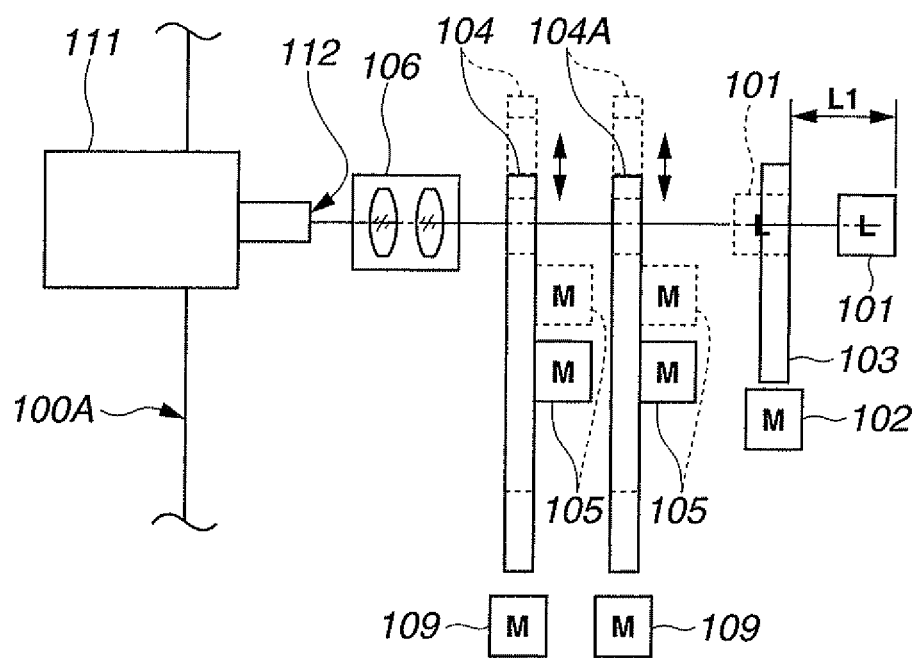
FIG. 2 is a view that describes another configuration example of an illumination portion of a light source device.
Figure 3:
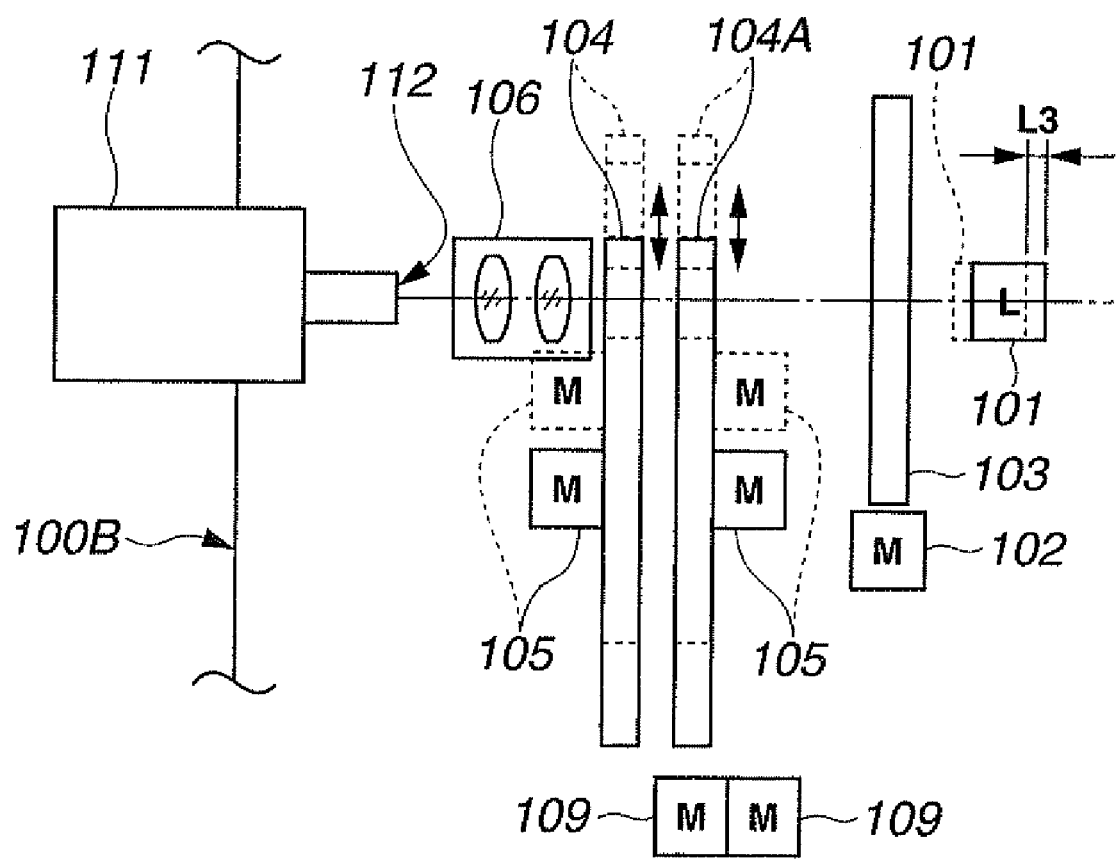
FIG. 3 is a view that describes a further configuration example of an illumination portion of a light source device.
Figure 4:
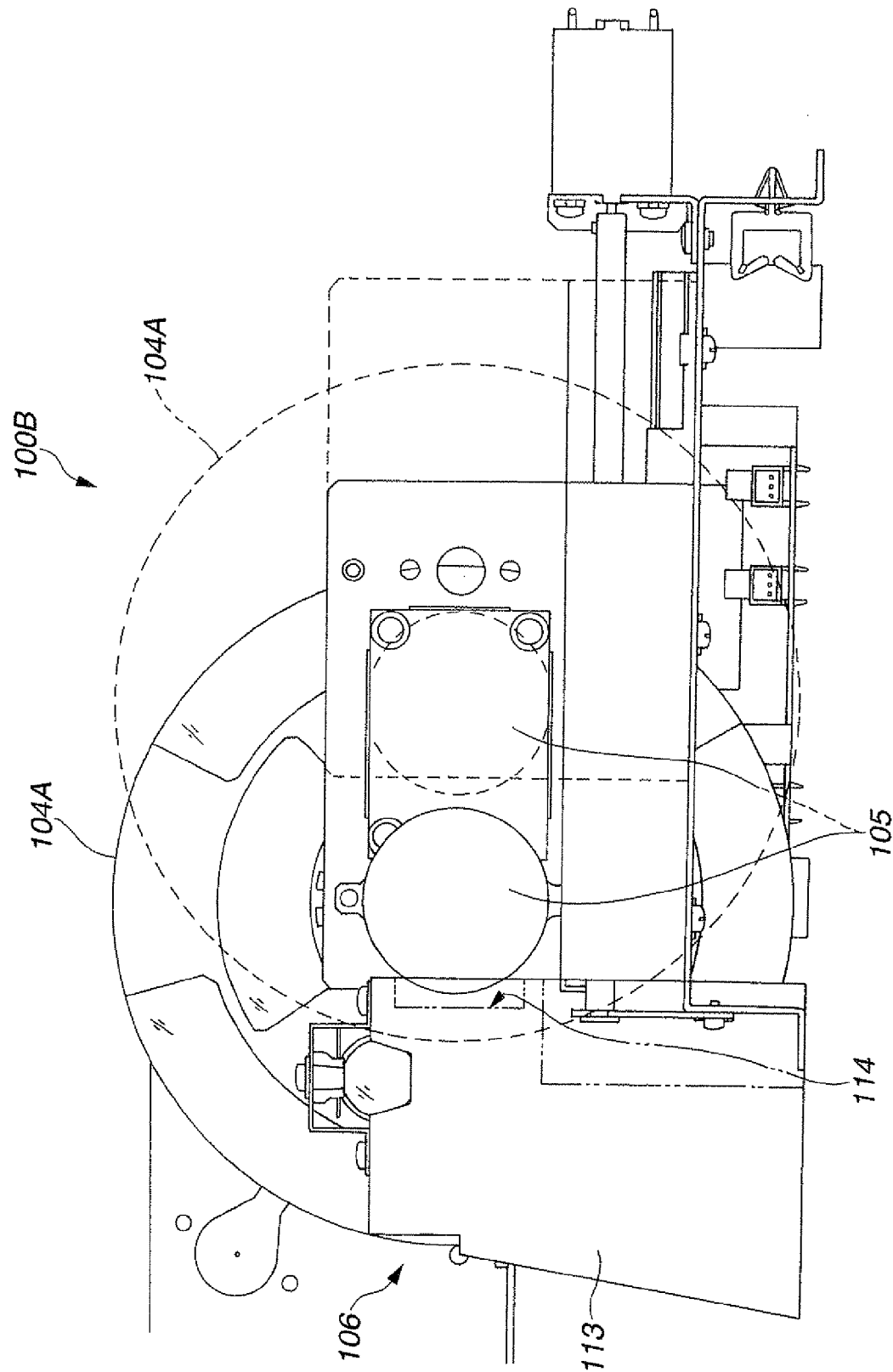
FIG. 4 is a view that describes the relation between a rotary filter and a lens base of the light source device shown in FIG. 3.
Figure 5:
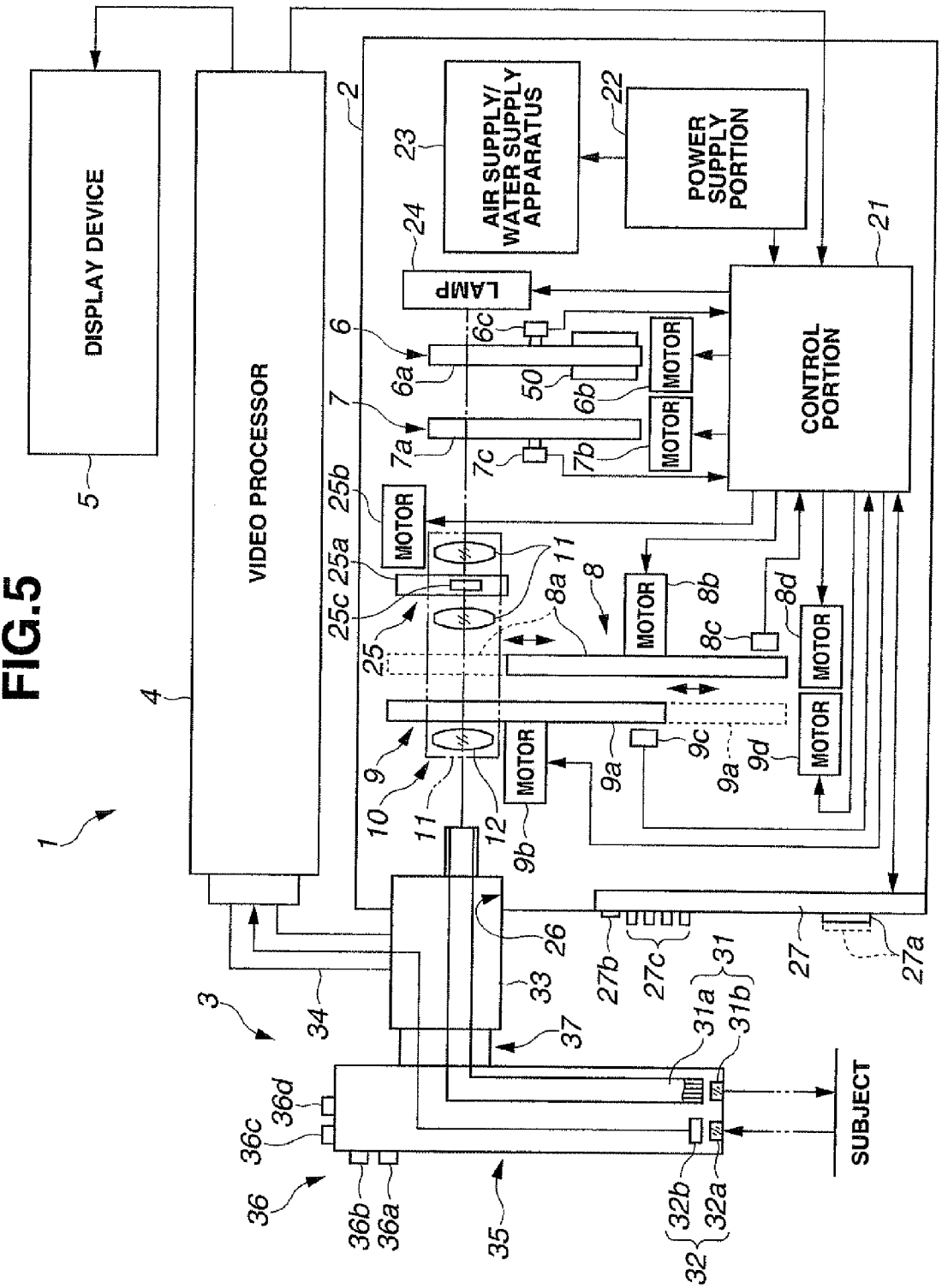
FIG. 5 is a block diagram that describes the configuration of an endoscope apparatus.

A light source device 2 according to the present embodiment that is shown in FIG. 5 is an external device of an endoscope 3. An endoscope system 1 further comprises a video processor 4 and a display device 5 such as an LCD as external devices.

The endoscope 3 is provided with an illumination optical system 31 and an observation optical system 32. The illumination optical system 31 comprises a light guide fiber 31a and an illumination lens group 311b. The observation optical system 32 comprises an observation lens group 32a and an image pickup device 32b such as a CCD as image pickup means.

An endoscope connector 33 that is detachably connected to a socket 26 of the light source device 2 is provided in the endoscope 3. An electric cable 34, for example, extends from the side of the endoscope connector 33 and is connected to the video processor 4.

An operation portion 36 is provided at a proximal end of an insertion portion 35 of the endoscope 3. The operation portion 36 has various buttons 36a, 36b, 36c, and 36d. Button 36a is an air supply/water supply button, button 36b is a suction button, button 36c is a freeze switch, and button 36d is a release switch.

The endoscope connector 33 is connected to a proximal end portion of a universal cord 37 that extends from the operation portion 36.

The video processor 4 internally comprises a drive circuit (not shown), a signal processing circuit (not shown), and a light control circuit (not shown). The drive circuit outputs a driving signal that drives the image pickup device 32b provided in the observation optical system 32 of the endoscope 3. The signal processing circuit generates and outputs a video signal corresponding to the display device 5 based on an image signal produced by photoelectric conversion and transmitted by the image pickup device 32b. The light control circuit outputs a modulated light signal that adjusts an aperture position of an aperture blade unit 25 to a control portion 21 of the light source device 2 that is described later, so that an image based on an image signal transmitted form the image pickup device 32b is the correct brightness.

An endoscopic image based on a video signal generated at the video processor 4 is displayed on the screen of the display device 5.

Figure 6:
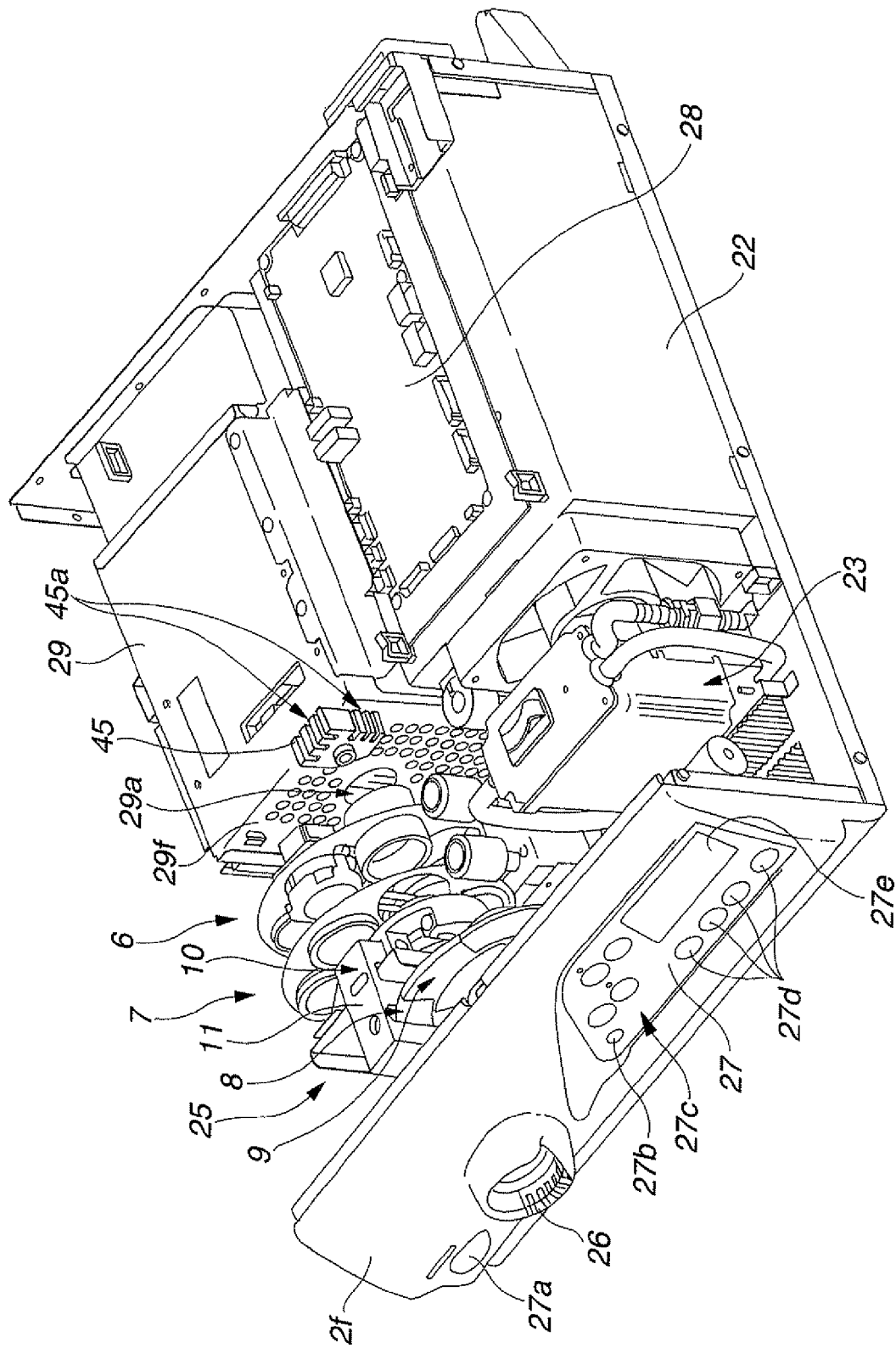
FIG. 6 is a view showing a state in which the top of the light source device is removed, and which illustrates the inner configuration of the light source device.

As illustrated in FIG. 5 and FIG. 6, the light source device 2 comprises the control portion 21, a power supply portion 22, an air supply/water supply apparatus 23, a light source lamp (hereafter, abbreviated as "lamp") 24, an aperture blade unit 25, a plurality of rotary devices for switching an observation light (hereafter, abbreviated as "rotary filter unit") 6, 7, 8, and 9, and a light-condensing device 10.

The light-condensing device 10 comprises a plurality of lenses 12 that are disposed in a lens holder 11. The rotary filter units 6, 7, 8, and 9 are disposed in the order of first rotary filter unit 6, second rotary filter unit 7, third rotary filter unit 8, and fourth rotary filter unit 9 from the lamp 24 side towards the light-condensing device 10.

In this connection, the control portion 21 is a control board 28, and the lamp 24 is provided inside a lamp shielding case 29 that serves as a housing.

According to the present embodiment, a first rotary plate 6a of the first rotary filter unit 6 and a second rotary plate 7a of the second rotary filter unit 7 are disposed opposite to each other. Further, a third rotary plate 8a of the third rotary filter unit 8 and a fourth rotary plate 9a of a fourth rotary filter unit 9 are disposed opposite to each other.

The rotary plate 6a and the rotary plate 7a are subjected to stop control in a state in which any one of optical filters, described later, is disposed in an illumination light path (hereafter, referred to as "optical path"). In contrast the rotary plate 8a and the rotary plate 9a are rotatingly controlled in a state in which they are disposed in the optical path and are subjected to stop control in a state in which they are outside the optical path.

The rotary plate 8a and the rotary plate 9a are provided in a removable condition in a rotary plate disposing space portion, described later, in the lens holder 11. An aperture disposing space portion, described later, is provided in the lens holder 11. The aperture blade unit 25 is provided in the aperture disposing space portion.

Reference numeral 29a denotes a light emission opening. The light emission opening 29a is formed at a predetermined position in a front face 29f of the lamp shielding case 29. When the lamp 24 is lighting, an illumination light is emitted through the light emission opening 29a in the direction of the socket 26. A heat absorbing portion 45 comprising a plurality of fins 45a as a heat releasing portion is provided at a predetermined position in the vicinity of the light emission opening 29a on the front face 29f. The heat absorbing portion 45 is, for example, formed with a metal that is a heat-absorbing member such as aluminum or stainless steel.

The light source device 2 includes the socket 26 and an operation panel 27 on the front panel 2f thereof. The operation panel 27 includes a power switch 27a, an emergency light display portion 27b, a lamp control setting display portion 27c, an illumination mode setting portion 27d, and an illumination mode display portion 27e.

The power switch 27a enters an "on" state when the power switch 27a is, for example, pushed inward from a position indicated by a dotted line to a position indicated by a solid line. When the power switch 27a is on, power is supplied to the light source device 2.

The emergency light display portion 27b lights when the lamp 24 burns out and switches to an emergency light. Further, the emergency light display portion 27b flashes when there is a malfunction such as the emergency light being burnt out, disconnected, or not mounted.

A lamp on/off switch and the like is provided in the lamp control setting display portion 27c. The lamp on/off switch is a switch for turning the lamp 24 on or off when the power switch 27a is on.

The illumination mode setting portion 27d is provided with a switch for selecting a plurality of illumination modes. The illumination mode display portion 27e notifies the user of the kind of observation light that is supplied to the illumination optical system, i.e. the optical filter that is disposed in the optical path of the lamp 24.

Hereunder, the specific configuration of the light source device 2 is described.

The control portion 21 of the light source device 2 shown in FIG. 5 supplies power to the rotary filter units 6, 7, 8, and 9 and the aperture blade unit 25. The control portion 21 also drivingly controls each of motors 6b, 7b, 8b, 8d, 9b, and 9d that comprise the respective rotary filter units 6, 7, 8, and 9, a motor 25c comprising the aperture blade unit 25, and an unshown pump inside the air supply/water supply apparatus 23.

An output voltage that is output from the control portion 21 is converted to a direct-current voltage by an unshown switching regulator that is a power supply stabilizer. The direct-current voltage is supplied to the lamp 24 and an emergency light 41 that is described later. The lamp 24 is, for example, a xenon lamp that utilizes electrical discharge in xenon gas. The spectrum of a xenon lamp closely resembles natural sunlight. Further, an illumination light that is emitted from a xenon lamp includes infrared light that is a heat source.

The first rotary filter unit 6 and the second rotary filter unit 7 will now be described.

The rotary filter units 6 and 7 respectively comprise a rotary plate, a drive motor, and a rotational position detection apparatus that are described later. The rotary plate is formed with a member that blocks light.

Figure 7:
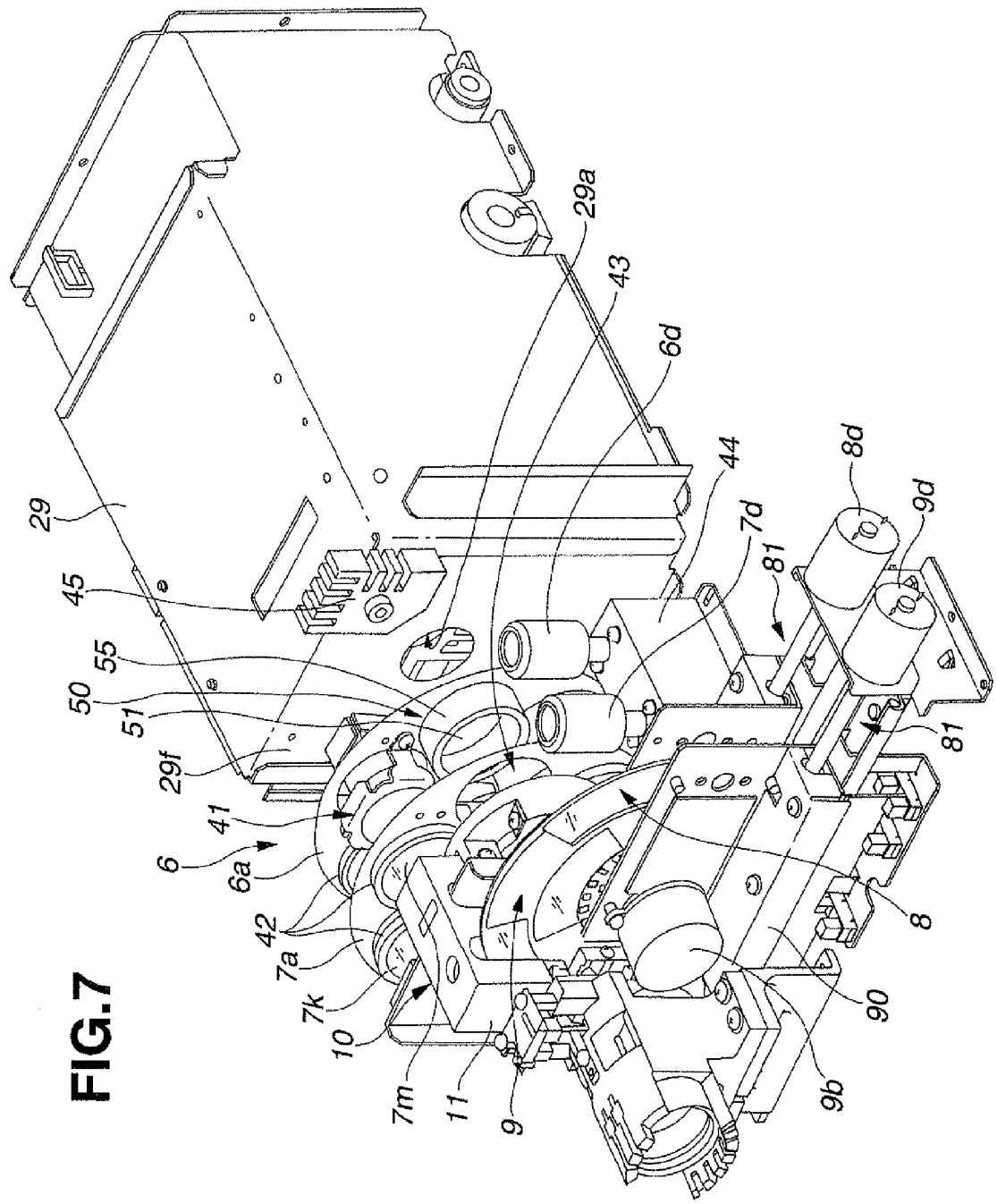
FIG. 7 is a view showing a state in which the front panel of the light source device is further removed, and which illustrates the configuration relating to illumination.
Figure 8:
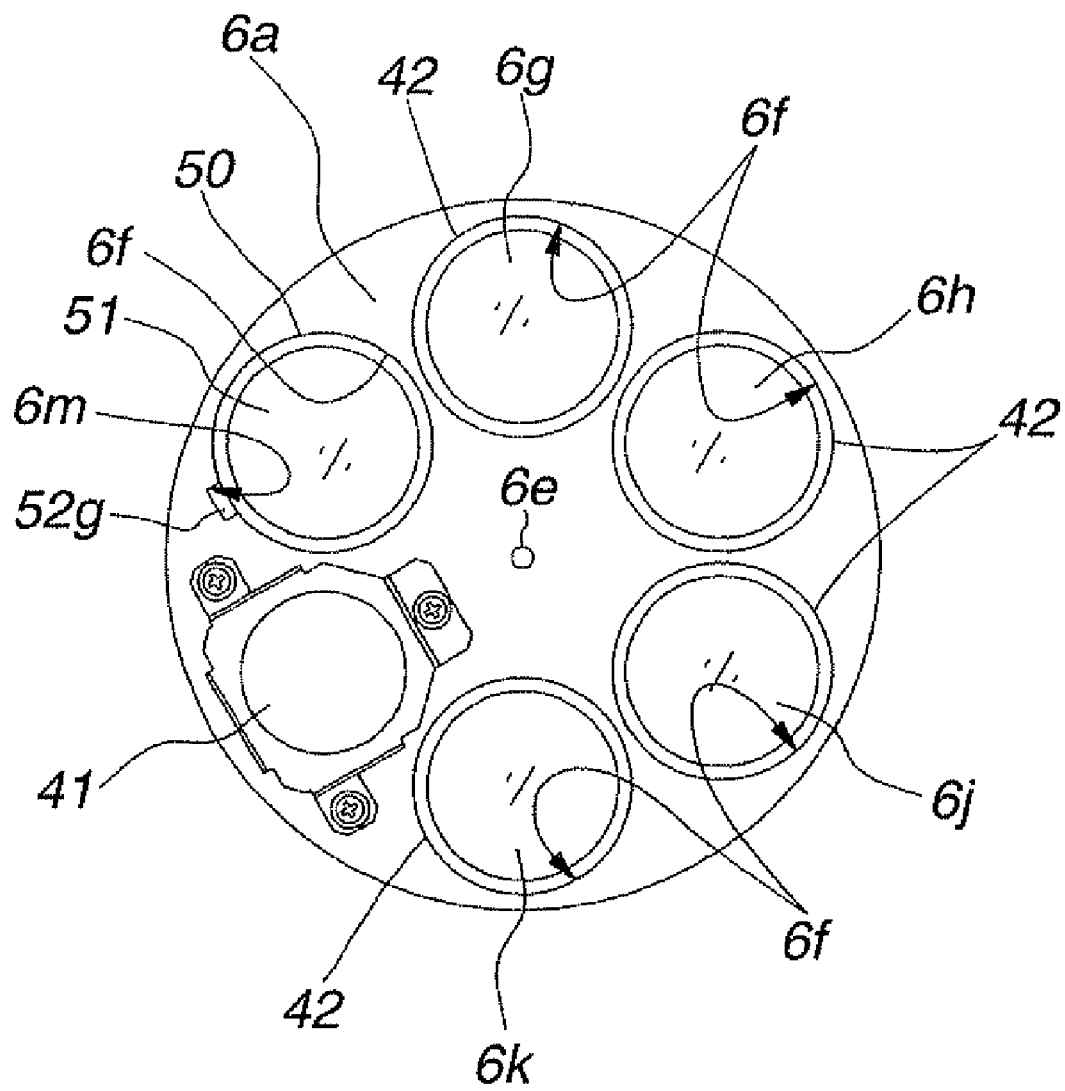
FIG. 8 is a view that describes the configuration of a first rotary plate.

As shown in FIG. 5, FIG. 7, and FIG. 8, the first rotary filter unit 6 includes a first rotary plate 6a, a first drive motor 6b, and a first rotational position detection apparatus (hereafter, abbreviated to "first rotation detecting apparatus"). For example, a worm gear 6d is provided on the drive shaft of the first drive motor 6b. The first rotary plate 6a is configured to rotate clockwise or counterclockwise accompanying rotation of the worm gear 6d. The first rotation detecting apparatus 6c is a potentiometer that comprises a position detecting base plate (not shown). The control portion 21 outputs a driving signal to the first drive motor 6b until detection of a voltage corresponding to a rotation position that is output from the first rotation detecting apparatus 6c.

As shown in FIG. 8, the first rotary plate 6a comprises a center hole 6e in which is disposed a rotating shaft (not shown), and a plurality of opening portions 6f. According to the present embodiment, for example, six of the opening portions 6f are provided at regular intervals in the circumferential direction. In addition to the emergency light 41, optical filters (hereafter, referred to as "filter") 51, 6g, 6h, 6j, and 6k are provided in the opening portions 6f, respectively. The filters 51, 6g, 6h, 6j, and 6k are, for example, in the clockwise direction starting after the emergency light 41, provided in the order of reflective filter 51, infrared light transmitting filter 6g, first fluorescent observation light transmitting filter (hereafter, referred to as "fluorescence filter") 6h, second fluorescence filter 6j, and third fluorescence filter 6k.

The reflective filter 51 prevents the supply of infrared light that is an unwanted heat source included in the illumination light to the endoscope. In other words, the reflective filter 51 is a filter that reflects infrared light. The reflective filter 51 is configured to be mounted via a filter mounting member 50, described later, in the opening portion 6f. The infrared light transmitting filter 6g is a filter for performing infrared light observation as one kind of special light observation. The first fluorescence filter 6h, the second fluorescence filter 6j, and the third fluorescence filter 6k are filters for performing fluorescent observation as one kind of special light observation. The filters 6g, 6h, 6j, and 6k are arranged so as to be mountable in a corresponding opening portion 6f via a filter fixing ring 42. Reference numeral 6m denotes, for example, a concave portion that is a disposition location setting portion. In a concave portion 6m is disposed a convex portion 52g, described later, that comprises the filter mounting member 50. In this connection, in a case where the disposition location setting portion is a convex portion, the filter mounting member 50 comprises a concave portion.

Figure 9:
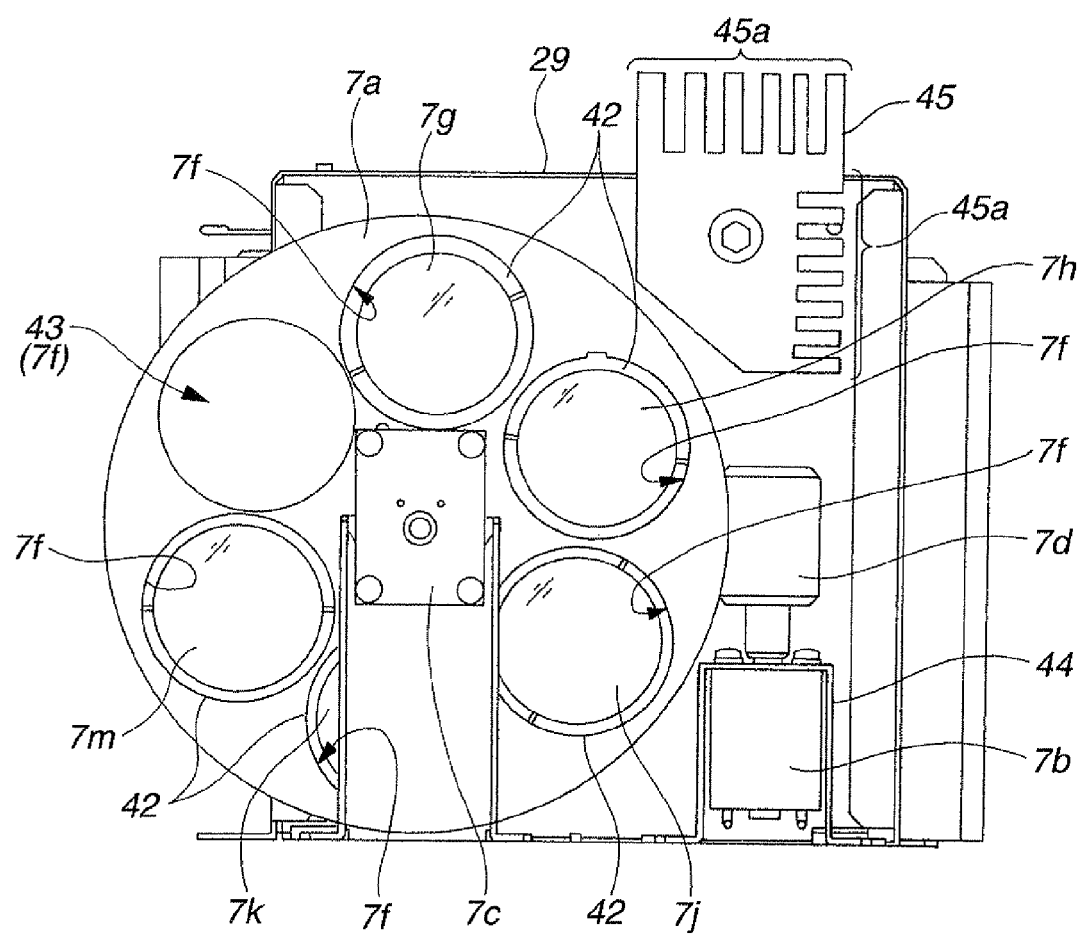
FIG. 9 is a view that describes the configuration of a second rotary filter unit.

As shown in FIG. 5, FIG. 7, and FIG. 9, the second rotary filter unit 7 comprises a second rotary plate 7a, a second drive motor 7b, and a second rotational position detection apparatus (hereafter, abbreviated as "second rotation detecting apparatus") 7c. A worm gear 7d is provided on the drive shaft of the second drive motor 7b. The second rotary plate 7a is configured to rotate accompanying rotation of the worm gear 7d. The second rotation detecting apparatus 7c is a potentiometer, similarly to the first rotation detecting apparatus 6c. The control portion 21 outputs a driving signal to the second drive motor 7b until detection of a voltage corresponding to a rotation position that is output from the first rotation detecting apparatus 7c. Reference numeral 44 denotes a motor case. The motors 6b and 7b are fixedly installed inside the motor case 44.

As shown in FIG. 9, the second rotary plate 7a comprises a center hole (not shown) and, for example, six opening portions 7f that are provided at regular intervals in the circumferential direction. One of the opening portions 7f is a through hole 43, that is, a through hole in which a filter is not provided. Optical filters 7g, 7h, 7j, 7k, and 7m are respectively provided in the opening portions 7f, for example, in that order in the clockwise direction starting from the through hole 43. The filter 7g is, for example, a narrow-band observation light transmitting filter (hereafter, described as "NBI filter"), the filter 7h is an ultraviolet light transmitting filter for performing ultraviolet light observation that is one kind of special light observation, and the filters 7j, 7k, and 7m are filters for performing other kinds of special light observation. Each of the filters 7g, 7h, 7j, 7k, and 7m is mounted to the respective opening portion 7f through a filter fixing ring 42.

The configuration of the filter mounting member 50 and mounting of the first rotary plate 6a of the reflective filter 51 to the opening portion 6f will now be described referring to FIG. 10 and FIG. 11.

First, the configuration of the filter mounting member 50 is described.

Figure 10:
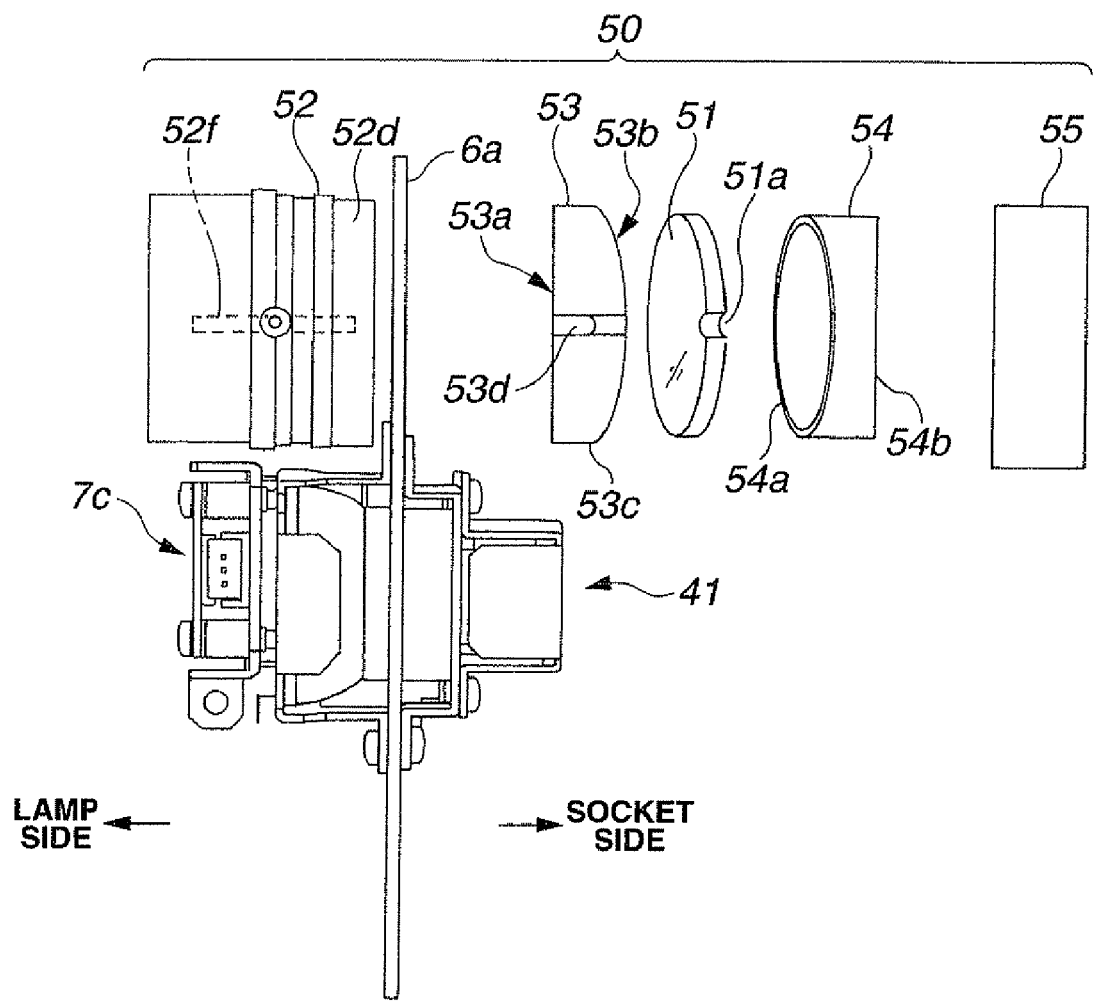
FIG. 10 is a view that describes the configuration of a filter mounting member.
Figure 11:
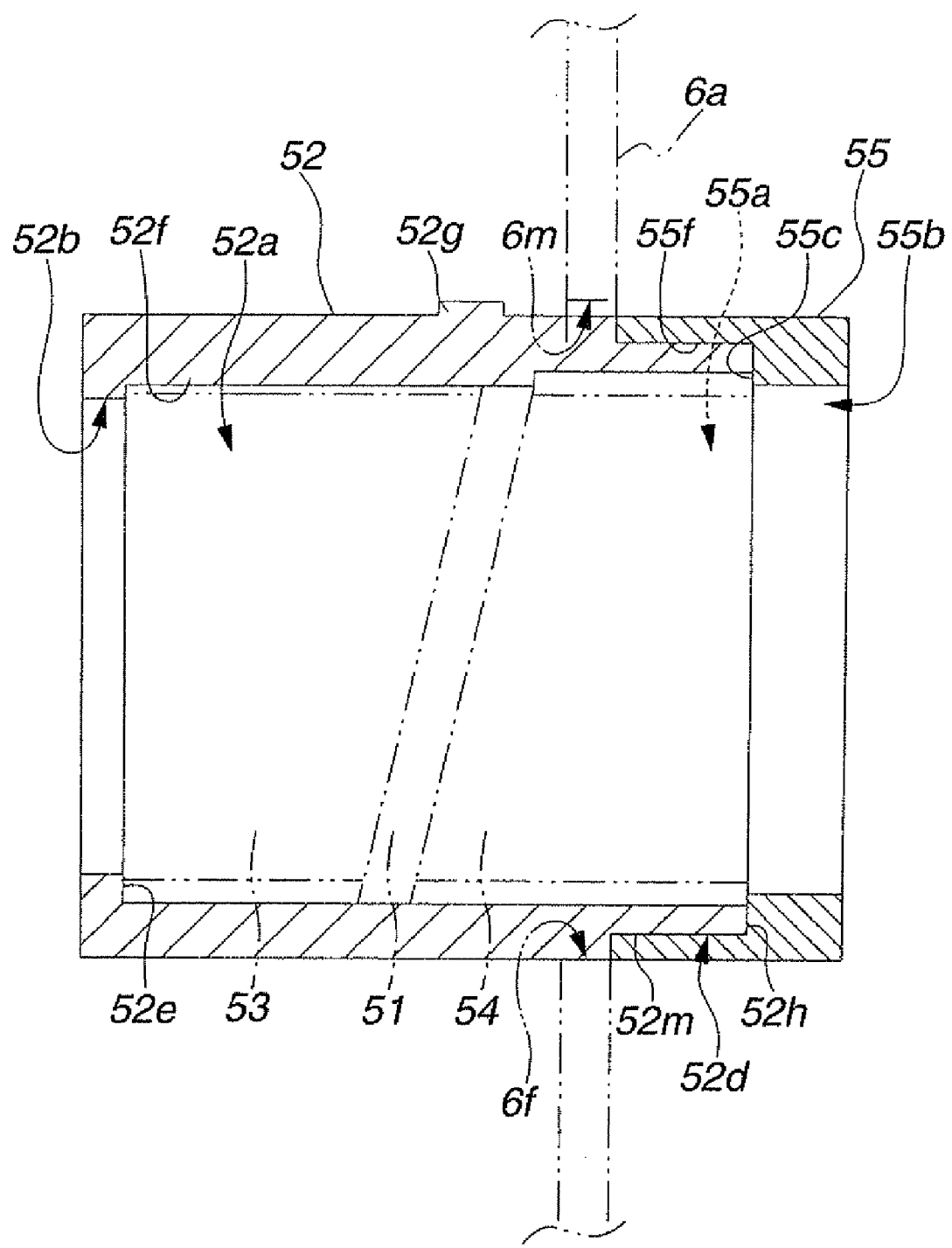
FIG. 11 is a view that describes a state in which a reflective filter is mounted in the first rotary plate by means of a filter mounting member.

As shown in FIG. 10 and FIG. 11, the filter mounting member 50 comprises a mounting portion main body (hereafter, abbreviated as "main body") 52, an inclination setting ring member (hereafter, abbreviated as "first ring") 53, the reflective filter 51, a filter presser member (hereafter, abbreviated as "second ring") 54, and a fastener 55.

The main body 52 is a cylindrical shape. The main body 52 mainly comprises a disposing space 52a, an incident opening 52b, and a fastener fixing portion 52d. The fastener fixing portion 52d comprises a male screw 52m on the outer circumference thereof. The main body 52 also serves as a heat absorbing portion and, for example, is made of a metal such as aluminum.

Inside the disposing space 52a are housed the first ring 53, the reflective filter 51, and the second ring 54. The incident opening 52b is a through hole that links the disposing space 52a with the outside. An illumination light that is emitted from the lamp 24 is incident to the incident opening 52b. The central axis of the incident opening 52b and the central axis of the disposing space 52a match. The inner diameter of the incident opening 52b is formed to be smaller than the inner diameter of the disposing space 52a. Accordingly, the disposing space 52a is equipped with a positioning face 52e, and a perpendicular end face 53a of the first ring 53 is arranged at the positioning face 52e.

On the inner circumferential surface of the disposing space 52a is provided a positioning protrusion 52f that has prescribed height dimensions and width dimensions. The positioning protrusion 52f is formed facing the direction of the main body opening from the positioning face 52e in parallel with the center axis. A convex portion 52g is provided at the outer circumferential face of the main body 52. The convex portion 52g is opposite to the positioning protrusion 52f. The convex portion 52g notifies the worker of the location of positioning protrusion 52f, and is also a reflection direction setting portion that is engageably disposed in the concave portion 6m that is formed in the opening portion 6f of the first rotary plate 6a.

The first ring 53 is a tubular member. The first ring 53 is disposed in the disposing space 52a of the main body 52. The first ring 53 comprises the perpendicular end face 53a and an inclined face 53b. The perpendicular end face 53a is formed as a face that is perpendicular to the central axis of the first ring 53. The perpendicular end face 53a is disposed in close contact with the positioning face 52e. The inclined face 53b is formed to incline at a predetermined angle with respect to the central axis of the first ring 53. The reflective filter 51 is disposed in close contact with the inclined face 53b. A positioning groove 53d that is parallel to the central axis is formed on the outer circumference 53c of the first ring 53. A positioning protrusion 52f is engageably inserted into the positioning groove 53d. The positioning groove 53d is formed at a predetermined position of the outer circumference 53c. The positioning groove 53d is a groove for positioning the reflective filter 51 that is disposed in close contact with the inclined face 53b inside the main body 52 in a condition in which the reflective filter 51 inclines in a predetermined direction with respect to the optical axis of the illumination light.

The second ring 54 is a tubular member. The second ring 54 is disposed in the disposing space 52a of the main body 52. The second ring 54 comprises a filter presser face 54a and a perpendicular end face 54b. The filter presser face 54a is an inclined face that contacts against the filter 51.

The fastener 55 is a cylindrical shape. The fastener 55 comprises an internal space 55a and an emission opening 55b. The emission opening 55b is a through hole that links the internal space 55a and the outside. A female screw 55f is formed in the inner circumferential face of the internal space 55a. The male screw 52m that is provided on the outer circumference of the main body 52 is screwed into the female screw 55f. The inner diameter of the emission opening 55b is less than the inner diameter of the internal space 55a. Further, the inner diameter of the emission opening 55b is less than the outer diameter dimensions of the second ring 54 and greater than the inner diameter dimensions thereof. That is, a bottom face 55c is configured to contact against the perpendicular end face 54b.

The process for assembling the filter mounting member 50 and the method of attaching the reflective filter 51 to the first rotary plate 6a will now be described.

First, the worker drops the first ring 53 inside the disposing space 52a of the main body 52. At that time, the worker causes the perpendicular end face 53a to oppose the positioning face 52e and also engages the positioning groove 53d with the positioning protrusion 52f. As a result, the first ring 53 is disposed such that the perpendicular end face 53a contacts against the positioning face 52e inside the disposing space 52a.

Next, the worker arranges the reflective filter 51 on the inclined face 53b of the first ring 53 that is disposed within the disposing space 52a of the main body 52. At this time, the worker engages a detent 51a that is provided in the reflective filter 51 with the positioning protrusion 52f. As a result, the reflective filter 51 is disposed on the inclined face 53b of the first ring 53.

Subsequently, the worker disposes the second ring 54 inside the disposing space 52a of the main body 52 in which the first ring 53 and the reflective filter 51 are disposed. At this time, an end on the perpendicular end face 54b side of the second ring 54 protrudes from an opening end 52h of the disposing space 52a. Here, the worker checks the protruding state of the second ring 54 from the opening end 52h and adjusts the position of the second ring 54. More specifically, the worker rotates the second ring 54 with respect to the disposing space 52a to achieve a state in which the entire filter presser face 54a contacts against the reflective filter 51. When positional adjustment of the second ring 54 is completed, the first ring 53, the reflective filter 51, and the second ring 54 are disposed in a predetermined state inside the disposing space 52a.

Next, the worker disposes the fastener 55 at the fastener fixing portion 52d of the main body 52 and tightens the fastener 55. Thereupon, the fastener 55 moves in the direction of the convex portion 52g and the bottom face 55c of the fastener 55 enters a fixed state in contact against the perpendicular end face 54b of the second ring 54. Thus, the filter mounting member 50 comprising the reflective filter 51 that is inclined at a predetermined angle is constructed.

Finally, the worker inserts the fastener 55 comprising the filter mounting member 50 into the opening portion 6f in which the concave portion 6m is formed from one side of the first rotary plate 6a. The worker then disposes the convex portion 52g comprising the filter mounting member 50 inside the concave portion 6m. In this disposition state, the worker applies an adhesive to a clearance between the opening portion 6f and the filter mounting member 50. As a result, the filter mounting member 50 comprising the reflective filter 51 is fixed in a preset state to a predetermined opening portion 6f of the first rotary plate 6a.

Figure 12:
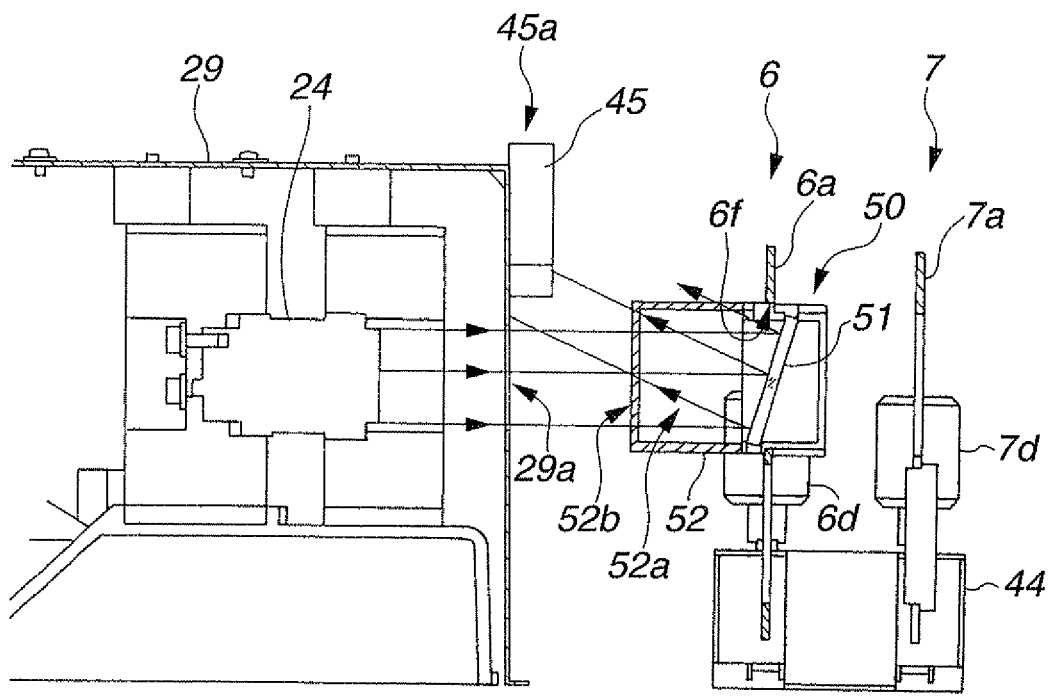
FIG. 12 is a view that illustrates the action of a reflective filter that is mounted in the first rotary plate by means of a filter mounting member.

As shown in FIG. 12, the reflective filter 51 provided in the first rotary plate 6a is disposed in the optical path of the lamp 24 and an illumination light is emitted from the lamp 24. The illumination light enters inside the disposing space 52a from the incident opening 52b of the main body 52 comprising the filter mounting member 50. Infrared light among the illumination light that enters the disposing space 52a is reflected by the reflective filter 51. The other visible light passes through the reflective filter 51 and continues in the direction of the second rotary plate 7a. One part of the infrared light that is reflected by the reflective filter 51 is radiated towards the inner circumferential face of the main body 52. The remaining part of the infrared light is radiated towards the heat absorbing portion 45 that is fixed at the front face 29f of the lamp shielding case 29 as shown in FIG. 9 and FIG. 12. As a result, the infrared light that is reflected by the reflective filter 51 is absorbed by the heat absorbing portion 45 and the main body 52 that also serves as a heat absorbing portion.

Thus, the filter mounting member provided with a reflective filter that is inclined at a predetermined angle is fixed in a predetermined state to an opening portion of a rotary plate. As a result, when the reflective filter is disposed in the optical path, the reflective filter is disposed in an inclined condition with respect to the optical axis of the illumination light facing a predetermined site. Therefore, an infrared light included in the illumination light that is emitted from the lamp is reflected towards a heat absorbing portion. Accordingly, it is possible to surely prevent deterioration of the lamp caused by infrared light returning as reflected light to the lamp and also prevent damage to electronic components or the like caused by radiation of infrared light.

Figure 13:
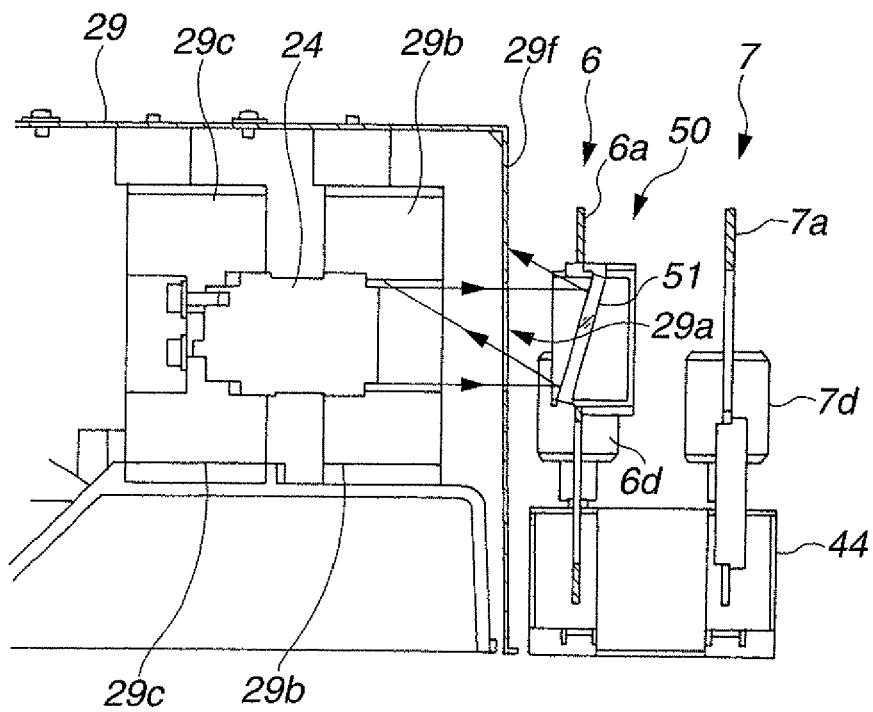
FIG. 13 is a view that illustrates a configuration in which infrared light that is reflected with the reflective filter is reflected towards a heat sink.

According to the present embodiment, infrared light that is reflected light is radiated towards the heat absorbing portion 45 and the main body 52 that also serves as a heat absorbing portion. However, the heat absorbing portion is not limited to these parts. For example, as shown in FIG. 13, a configuration may be adopted in which a heat sink 29b to which is mounted the lamp 24 that is provided inside the lamp shielding case 29 is employed as a heat absorbing portion. As a result, the length dimensions of the main body 52 can be shortened and the first rotary plate 6a can be brought adjacent to the front face 29f of the lamp shielding case 29 to thereby reduce the size of the light source device. Further, a heat absorbing portion may be provided as the front face 29f of the lamp shielding case 29 or an unshown top plate comprising the light source device 2.

The third rotary filter unit 8 and the fourth rotary filter unit 9 will now be described.

Each of the rotary filter units 8 and 9 principally comprise a rotary plate, a rotary motor, a base plate, and a forward/rearward movement motor. The rotary plate is formed with a member that blocks light.

As shown in FIG. 5, FIG. 14, FIG. 15, and FIG. 16, the third rotary filter unit 8 comprises a third rotary plate 8a, a first rotary motor 8b, a first base plate 8c, and a first forward/rearward movement motor 8d. The first rotary motor 8b is integrally fixed to the first base plate 8c. The first forward/rearward movement motor 8d moves the first base plate 8c forward or rearward in the optical path direction.

The first rotary motor 8b is integrally fixed to the first base plate 8c, and a drive shaft (not shown) of the first rotary motor 8b is fixed to a center hole 8f of the third rotary plate 8a. Accordingly, the third rotary plate 8a is configured to be rotated in a predetermined direction accompanying rotational driving of the first rotary motor 8b.

Figure 16:
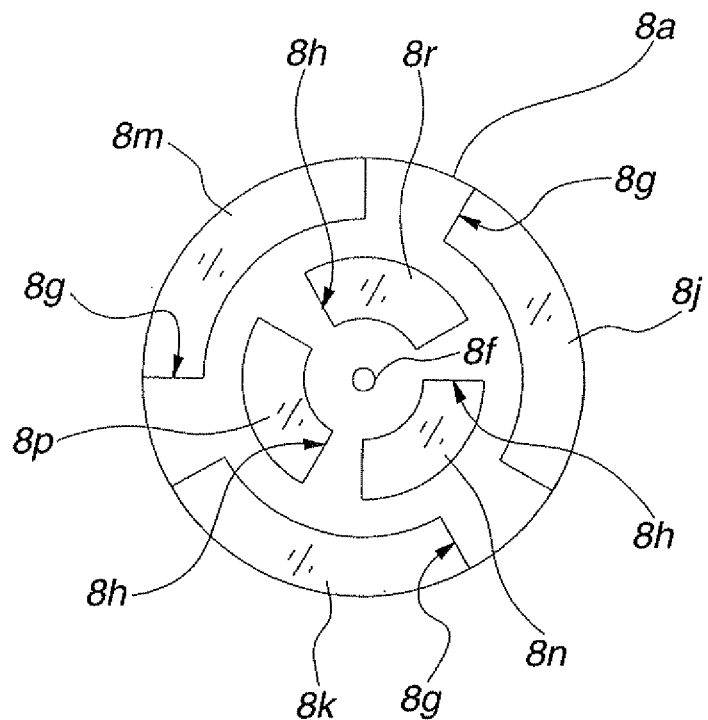
FIG. 16 is a view that illustrates the configuration of a third rotary plate.

As shown in FIG. 16, the third rotary plate 8a comprises the center hole 8f, and comprises a plurality of outer circumferential opening portions 8g and a plurality of inner circumferential opening portions 8h around the center hole 8f. More specifically, the third rotary plate 8a is a double filter structure that comprises the plurality of outer circumferential opening portions 8g on the outer circumference side and comprises the plurality of inner circumferential opening portions 8h on the inner circumference side.

In the outer circumferential opening portions 8g are provided an R filter 8j, a G filter 8k, and a B filter 8m as optical filters that transmit light of the wavelengths of red, green, and blue, respectively. The inner circumferential opening portions 8h are provided with a first narrow-band light transmitting filter 8n, a second narrow-band light transmitting filter 8p, and a third narrow-band light transmitting filter 8r that respectively transmit narrow-band light of a predetermined wavelength.

A rotation control board 8e on which unshown electronic components are fitted is mounted on the first base plate 8c. The rotation control board 8e comprises a circuit that detects the rotation position and rotational speed of the third rotary plate 5a and a circuit that outputs a detection signal thereof to the control portion 21.

The first base plate 8c and the first forward/rearward movement motor 8d are connected through a forward/rearward movement mechanism 80. The first forward/rearward movement mechanism 80 comprises a feed screw 81, a feed nut 83, a nut fixing portion 84, and a movement control board 86. The feed screw 81 comprises a screw part 82. The screw part 82 is screwed into the feed nut 83. The nut fixing portion 84 fixes the feed nut 83 to a predetermined position of the first base plate 8c. Electronic components such as movement position detection sensors 85a, 85b, and 85c are mounted on the movement control board 86. The third rotary plate 8a is moved forward or rearward with respect to the optical path accompanying driving of the forward/rearward movement motor 8d.

Figure 14:
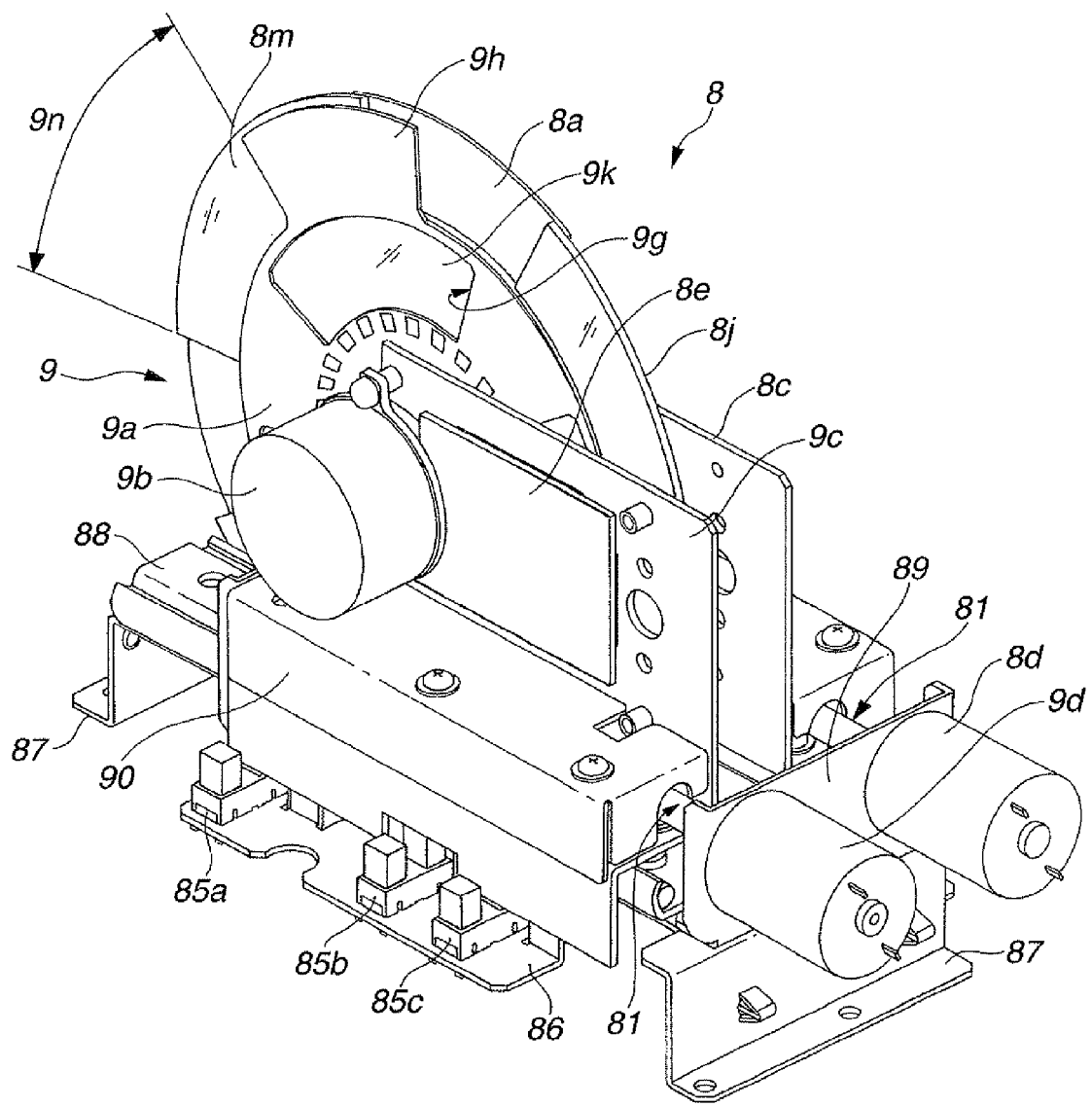
FIG. 14 is a view that illustrates the configuration of a third rotary filter unit and a fourth rotary filter unit.
Figure 15:
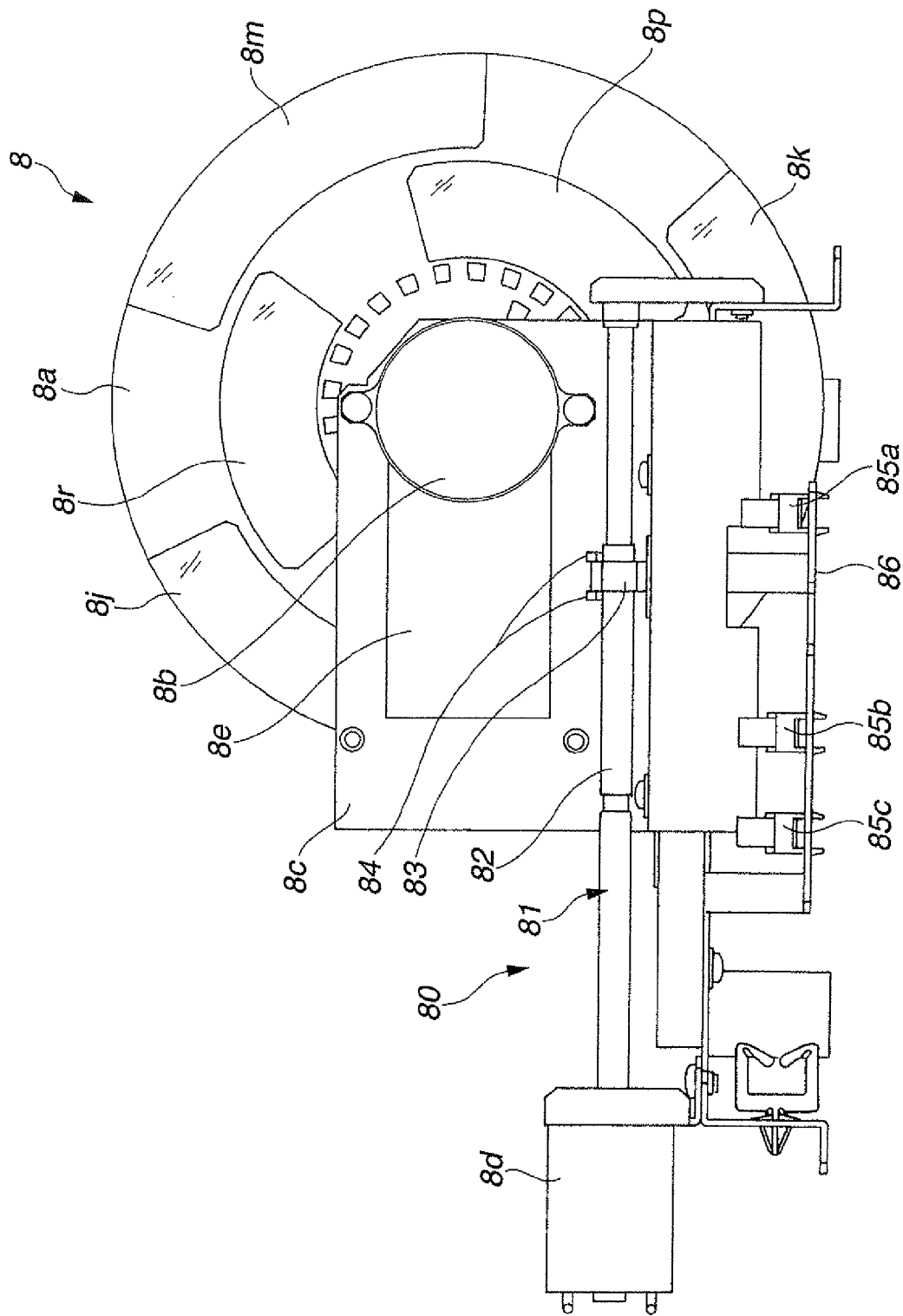
FIG. 15 is a view that illustrates the configuration of the third rotary filter unit.
Figure 17:
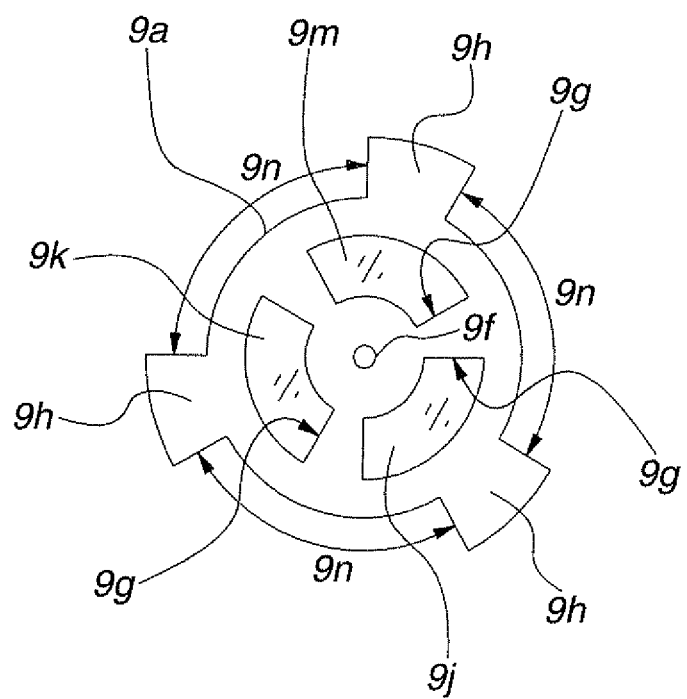
FIG. 17 is a view that illustrates the configuration of a fourth rotary plate.

As shown in FIG. 5, FIG. 14, and FIG. 17, the fourth rotary filter unit 9 comprises a fourth rotary plate 9a, a second rotary motor 9b, a second base plate 9c, and a second forward/rearward movement motor 9d. The second rotary motor 9b is integrally fixed to the second base plate 9c. The second forward/rearward movement motor 9d moves the second base plate 9c forward or rearward in the optical path direction.

The second rotary motor 9b is integrally fixed to the second base plate 9c. A drive shaft (not shown) of the second rotary motor 9b is fixed to a center hole 9f of the fourth rotary plate 9a. Accordingly, the fourth rotary plate 9a is configured to be rotated in a predetermined direction accompanying rotational driving of the second rotary motor 9b.

An unshown rotation control board 9e is mounted on the second base plate 9c. Further, the second base plate 9c and the second forward/rearward movement motor 9d are connected through the forward/rearward movement mechanism 80.

As shown in FIG. 17, the fourth rotary plate 9a comprises a center hole 9f, and comprises a plurality of opening portions 9g corresponding to the inner circumferential opening portions 8h around the center hole 9f. A plurality of shutter portions 9h that are formed with a predetermined width at regular intervals from each other are provided on the outer circumference. In the opening portions 9g are provided a first excitation filter 9j, a second excitation filter 9k, and a third excitation filter 9m that, for example, respectively transmit an excitation light of a predetermined wavelength.

More specifically, the fourth rotary plate 9a according to the present embodiment is a rotary plate that serves as both a shutter and a filter, and comprises a plurality of shutter portions 9h and a plurality of opening portions 9g. An opening formed between a shutter portion 9h and a shutter portion 9h represents a light transmittance range 9n that the illumination light passes through. Thus, as shown in FIG. 14, by synchronously controlling the two rotary plates 8a and 9a under control of the control portion 21 to displace the shutter portions 9h, for example, by a predetermined amount with respect to filters 8j, 8k, and 8m of the outer circumferential opening portions 8g that are provided in the third rotary plate 8a, the light transmittance range 9n through which the illumination light actually passes can be suitably set and changed.

The first base plate 8c comprising the third rotary filter unit 8 and the second base plate 9c comprising the fourth rotary filter unit 9 are slidingly disposed, respectively, on a pair of rails 88 provided on the filter unit disposing base 87 that is integrally fixed to the light source device 2 as shown in FIG. 14. The first forward/rearward movement motor 8d and the second forward/rearward movement motor 9d are integrally fixed, respectively, to a motor fixing portion 89 provided in the filter unit disposing base 87.

The third rotary plate 8a is moved forward or rearward accompanying driving of the forward/rearward movement motor 8d. When the sensors 85a, 85b, and 85c are photointerrupters, the forward/rearward movement motor 8d moves the third rotary plate 8a to a predetermined position with respect to the optical path based on a combination (refer to Table 1 described later) of output results (blocking light/not blocking light) that are output from the respective sensors 85a, 85b, and 85c. More specifically, for example, in the case of a combination in which the output results from the sensors 85a and 85b are "blocking light" and the result from the sensor 85c is "not blocking light", the inner circumferential opening portion 8h provided at an inner circumferential portion of the third rotary plate 8a is disposed in the optical path by the forward/rearward movement motor 8d. Further, in the case of a combination in which the results from the sensors 85a and 85c are "blocking light" and the result from the sensor 85b is "not blocking light", the outer circumferential opening portion 8g provided at an outer circumferential portion of the third rotary plate 8a is disposed in the optical path by the forward/rearward movement motor 8d. Furthermore, in the case of a combination in which the results from the sensors 85a and 85b are "not blocking light" and the result from the sensor 85c is "blocking light", the third rotary plate 8a is withdrawn from the optical path by the forward/rearward movement motor 8d.

| Sensor | | | Relation between rotary plate and |
| --- | --- | --- | --- |
| 85a | 85b | 85c | optical path |
| Blocking light | Blocking light | Not blocking light | Inner circumferential portion of rotary plate is disposed in optical path |
| Blocking light | Not blocking light | Blocking light | Outer circumferential portion of rotary plate is disposed in optical path |
| Not blocking light | Not blocking light | Blocking light | Rotary plate is withdrawn from optical path |

The fourth rotary plate 9a is moved forward or rearward accompanying driving of the forward/rearward movement motor 9d. When the sensors 85a, 85b, and 85c are photointerrupters, the forward/rearward movement motor 9d also moves the fourth rotary plate 9a to a predetermined position with respect to the optical path based on the combinations shown in Table 1 as output results that are output from the respective sensors 85a, 85b, and 85c. More specifically, for example, in the case of a combination in which the output results from the sensors 85a and 85b are "blocking light" and the result from the sensor 85c is "not blocking light", an opening portion 9g provided at an inner circumferential portion of the fourth rotary plate 9a is disposed in the optical path by the forward/rearward movement motor 9d. Further, in the case of a combination in which the results from the sensors 85a and 85c are "blocking light" and the result from the sensor 85b is "not blocking light", a shutter portion 9h provided at an outer circumferential portion of the fourth rotary plate 9a is disposed in the optical path by the forward/rearward movement motor 9d. Furthermore, in the case of a combination in which the results from the sensors 85a and 85b are "not blocking light" and the result from the sensor 85c is "blocking light", the fourth rotary plate 9a is withdrawn from the optical path by the forward/rearward movement motor 9d.

Reference numeral 90 denotes a cover, The cover 90 protects the forward/rearward movement mechanism 80 and also prevents dust from attaching to the screw part 82 of the feed screw 81 or the feed nut 83 or the like.

Figure 18:
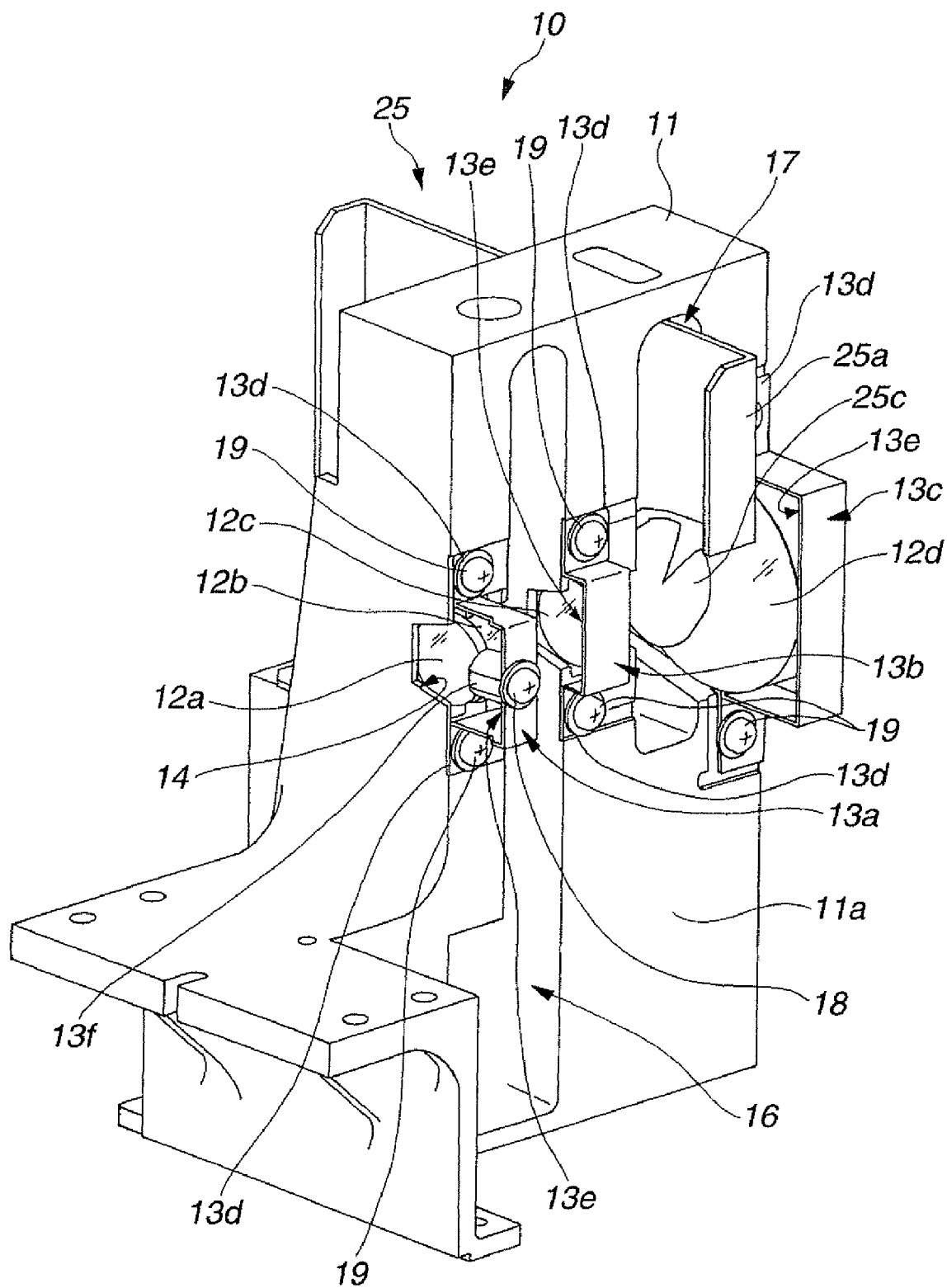
FIG. 18 is an oblique perspective view that illustrates the configuration of a light-condensing device.
Figure 19:
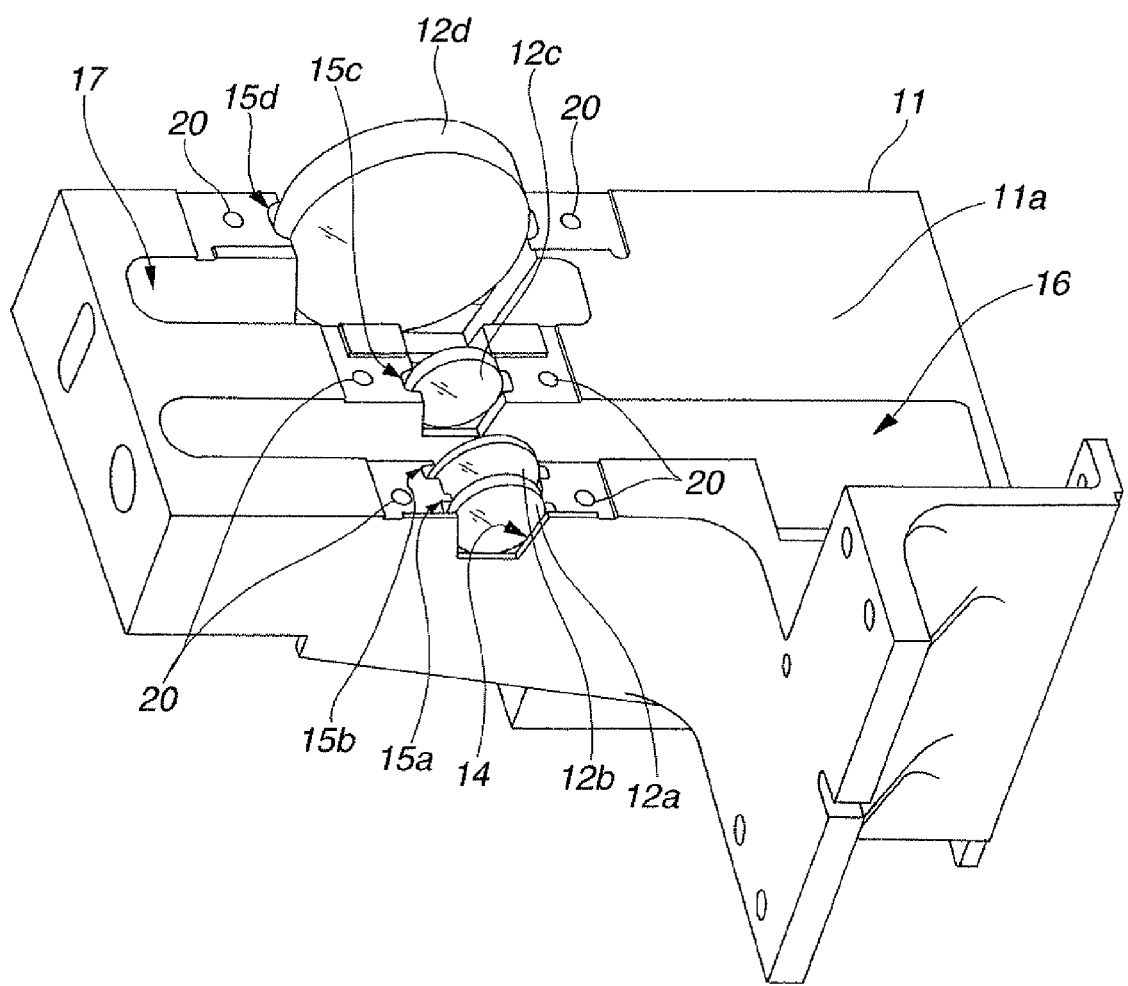
FIG. 19 is a view that illustrates a lens holder in which a plurality of optical lenses are disposed.

As shown in FIG. 18 and FIG. 19, the light-condensing device 10 comprises a lens holder 11, lenses 12a, 12b, 12c, and 12d, for example, as a plurality of optical lenses, lens retainers 13a, 13b, and 13c as lens holding members, and an aperture blade unit 25. The lens retainers 13a, 13b, and 13c are formed in correspondence with the outer diameter and thickness of the lenses 12a, 12b, 12c, and 12d. The lens retainers 13a, 13b, and 13c comprise a pair of fixing portions 13d having a hole that a screw 19 passes through and a retainer portion 13e, and are formed in a predetermined curve shape. The lens retainer 13a is a lens retainer that fixes the lenses 12a and 12b, and the retainer portion 13e has a through hole through which a fixing screw 18 that fixes the lenses 12a and 12b passes.

As shown in FIG. 19, in the lens holder 11 are formed an optical path formation groove 14, lens disposition concave portions 15a, 15b, 15c, and 15d in which lenses 12a, 12b, 12c, and 12d are respectively disposed, a rotary plate disposing space portion 16 in which rotary plates 8a and 9a that are moved forward and rearward by the forward/rearward movement motors 8d and 9d are disposed, and an aperture disposing space portion 17 in which an aperture plate 25a comprising the aperture blade unit 25 is disposed. Reference numeral 20 denotes a screw hole. The screw holes 20 are formed one by one at predetermined positions that sandwich the optical path formation groove 14. Screws 19 (see FIG. 18) for fixing the lens retainers 13a, 13b, and 13c to the lens holder 11 are screwed into the screw holes 20.

The optical path formation groove 14 is a substantially trapezoidal shape. The optical path formation groove 14 is formed in a straight line shape on one side face 11a of the lens holder 11. The optical path formation groove 14 is formed towards the side of the rotary plates 8a and 9a that move the opening forward and rearward. The shape of the lens disposition concave portions 15a, 15b, 15c, and 15d, that is, the width dimensions, depth dimensions, and length dimensions, is set based on the diametrical dimensions and thickness dimensions of the lenses that are respectively provided in the lens disposition concave portions 15a, 15b, 15c, and 15d. More specifically, the configuration is such that when the lenses 12a, 12b, 12c, and 12d are respectively disposed in the corresponding lens disposition concave portions 15a, 15b, 15c, and 15d, one part of the outer circumferential part of the lenses 12a, 12b, 12c, and 12d protrudes to outside from the opening of the optical path formation groove 14 such that the optical axis of the lenses 12a, 12b, 12c, and 12d matches the optical axis of the illumination light.

When fixedly providing each of the lenses 12a, 12b, 12c, and 12d in the lens holder 11, the worker places the lens holder 11 in a sideways state as shown in FIG. 19, i.e. places the opening of the optical path formation groove 14 facing upward as viewed in the figure. The worker then arranges the lenses 12a, 12b, 12c, and 12d so that they drop into the lens disposition concave portions 15a, 15b, 15c, and 15d corresponding to the respective lenses.

Next, the worker covers lenses 12a and 12b that are arranged in the lens disposition concave portions 15a and 15b with the lens retainer 13a and fixes the lens retainer 13a to the lens holder 11 with screws 19. The worker then inserts the fixing screw 18 through the through hole of the retainer portion 13e and screws the fixing screw 18 into a spacer 13f having a female screw. Thereupon, one end face of the fixing screw 18 that protrudes from the spacer 13f contacts against and presses the lenses 12a and 12b to thereby integrally fix the lenses 12a and 12b in the lens holder 11. Further, the worker covers the lens 12c that is arranged in the lens disposition concave portion 15c with the lens retainer 13b and fixes the lens retainer 13b in the lens holder 11 with screws 19. Thereupon, the lens 12c is integrally fixed in the lens holder 11 by the lens retainer 13b. Similarly, the worker covers the lens 12d that is arranged in the lens disposition concave portion 15d with the lens retainer 13c and fixes the lens retainer 13c in the lens holder 11 with screws 19 to integrally fix the lens 12d in the lens holder 11 by means of the lens retainer 13c.

Thus, the lenses 12a, 12b, 12c, and 12d are integrally fixed in the lens holder 11. In this fixed state, one part of the outer circumferential portions of the lenses 12a, 12b, 12c, and 12d protrudes to the side on which are arranged the rotary plates 8a and 9a that are moved forward and rearward from the one side face 11a of the lens holder 11.

As shown in FIG. 5 and FIG. 18, the aperture blade unit 25 comprises an aperture plate 25a, an aperture blade 25b, and a pulse motor 25c. The aperture blade 25b is arranged so as to be disposed in the optical path. The pulse motor 25c is driven based on a control signal that is generated and output at the control portion 21 on the basis of a modulated light signal that is output from the video processor 4 to the control portion 21. More specifically, when a light amount is insufficient, the aperture blade 25b is operated so as to increase the light amount that passes through a notch of the aperture blade 25b by driving of the pulse motor 25c. Conversely, when there is an excessive amount of light, the aperture blade 25b is operated so as to reduce the light amount that passes through the notch of the aperture blade 25b by driving of the pulse motor 25c.

Figure 20:
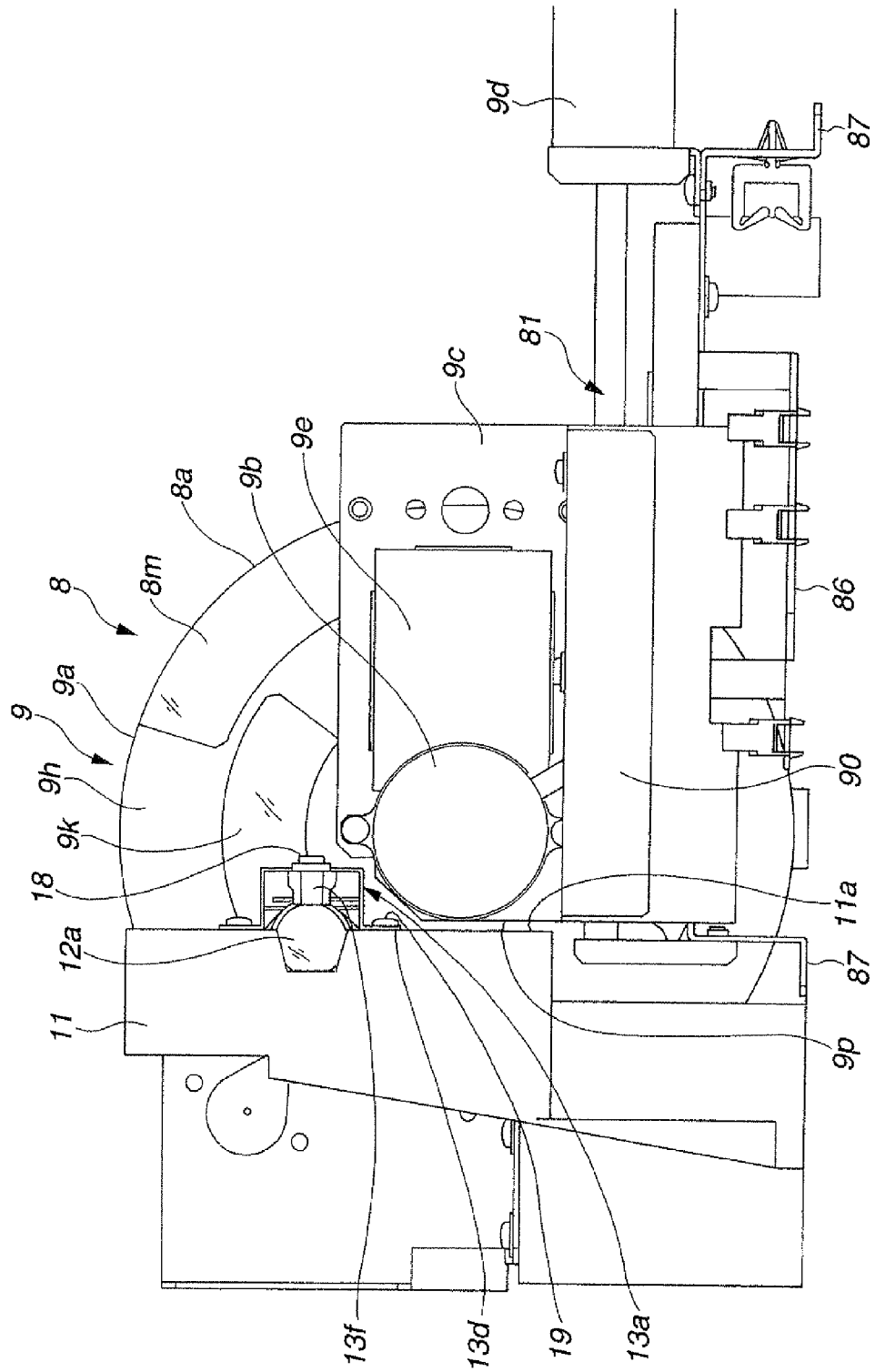
FIG. 20 is a view that illustrates the relation between the light-condensing device and the third rotary filter unit and fourth rotary filter unit.

The relation between the light-condensing device 10 and the third rotary filter unit 8 and fourth rotary filter unit 9 will now be described referring to FIG. 20.

In the light source device 2 of the present embodiment, the lenses 12a, 12b, 12c, and 12d protrude in a predetermined direction from the one side face 11a of the lens holder 11. As a result, as shown in FIG. 20, when unshown filters 8n, 8p, and 8r provided in the third rotary plate 8a or filters 9j, 9j, 9k provided in the fourth rotary plate 9a are disposed in the optical path, one side face 9p of the second base plate 9c is disposed adjacent to the one side face 11a of the lens holder 1.

Consequently, without providing a motor relief part in the lens holder 11, a distance from the center of the fourth rotary plate 9a to the center of the lens 12a is shorter than a distance from the center of a rotary filter of the conventional light source device to the center of a lens thereof.

Thus, by making the lenses of the light-condensing device protrude from one side face of the lens holder in a direction in which the filter unit is provided, the rotary motor is brought adjacent to the one side face of the lens holder comprising the light-condensing device, and it is possible to make a distance from the center of the rotary plate to the center of the lens shorter than the distance from the center of a rotary filter of the conventional light source device to the center of a lens thereof. It is therefore possible to decrease the diameter of the rotary plate or to provide three filters in the rotary plate.

It is thus possible to achieve a further reduction in the size of the light source device or provide a light source device that enables observation by many kinds of special light irrespective of the small size of the device.

A method of arranging the lenses 12a, 12b, 12c, and 12d in the lens holder 11 is not limited to the method described in the above embodiment. For example, as shown in FIG. 21, a configuration may be adopted in which the lenses 12a, 12b, 12c, and 12d are arranged in lens holding members 91, 92, and 93, and the lens holding members 91, 92, and 93 in which the lenses 12a, 12b, 12c, and 12d are arranged are then fixed to a lens holder 11A with, for example, screws 99.

Figure 21:
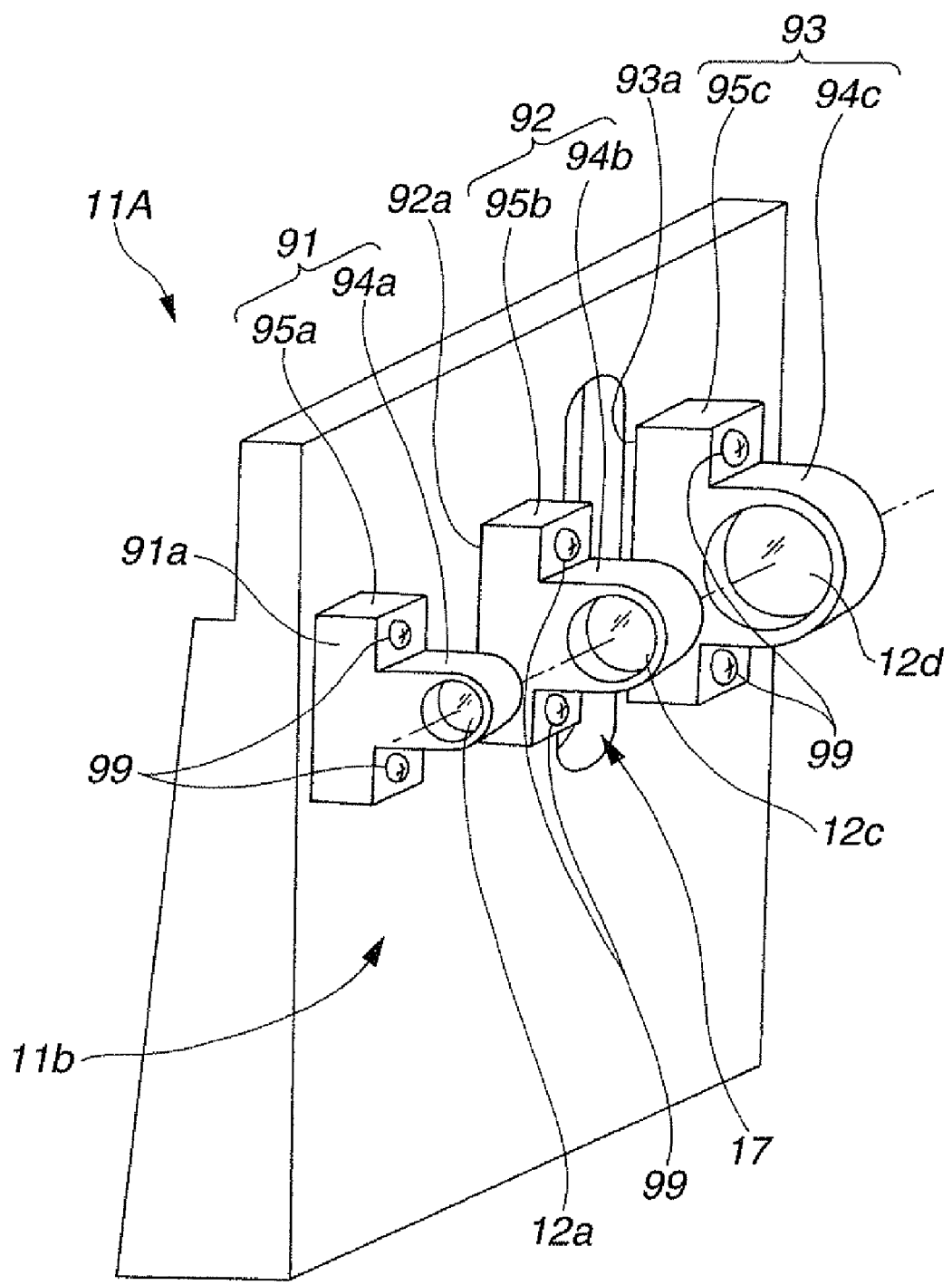
FIG. 21 is a view that illustrates another configuration example of a lens holder in which a plurality of optical lenses are disposed.

As shown in FIG. 21, the lens holder 11A of the present embodiment comprises one side face 11b. At predetermined positions on a flat surface of the one side face 11b, the lens holding members 91, 92, and 93 are fixed by screws 99. The lens holding member 91 comprises a lens disposing portion 94a and a pair of convex portions 95a. The lens holding member 92 comprises a lens disposing portion 94b and a pair of convex portions 95b. The lens holding member 93 comprises a lens disposing portion 94c and a pair of convex portions 95c. In the convex portions 95a, 95b, and 95c are formed through holes (not shown) through which are passed screws 99 that are screwed into unshown screw holes that are formed in the one side face 11b.

The width dimensions and thickness dimensions of the lens disposing portions 94a, 94b, and 94c are set based on the diametrical dimensions and thickness dimensions of the lenses to be disposed therein. The height dimensions of the convex portions 95a, 95b, and 95c are the same, and in the present embodiment the width dimensions of the convex portions 95a, 95b, and 95c differ.

The distances from mounting surfaces 91a, 92a, and 93a of the lens holding members 91, 92, and 93 that are mounted on the one side face 11b to the optical axis of each lens 12a, 12b, 12c, and 12d are set to the same dimensions. According to the present embodiment, the lenses 12a and 12b are arranged in the lens holding member 91, the lens 12c is arranged in the lens holding member 92, and the lens 12d is arranged in the lens holding member 93.

A clearance between the lens holding member 91 and the lens holding member 92 is configured to be the same as the width dimensions of the rotary plate disposing space portion 16. More specifically, the rotary plates 8a and 9a can move forward and rearward between the lens holding member 91 and the lens holding member 92. That is, the lens holder 11A comprises only the aperture disposing space portion 17.

Figure 22:
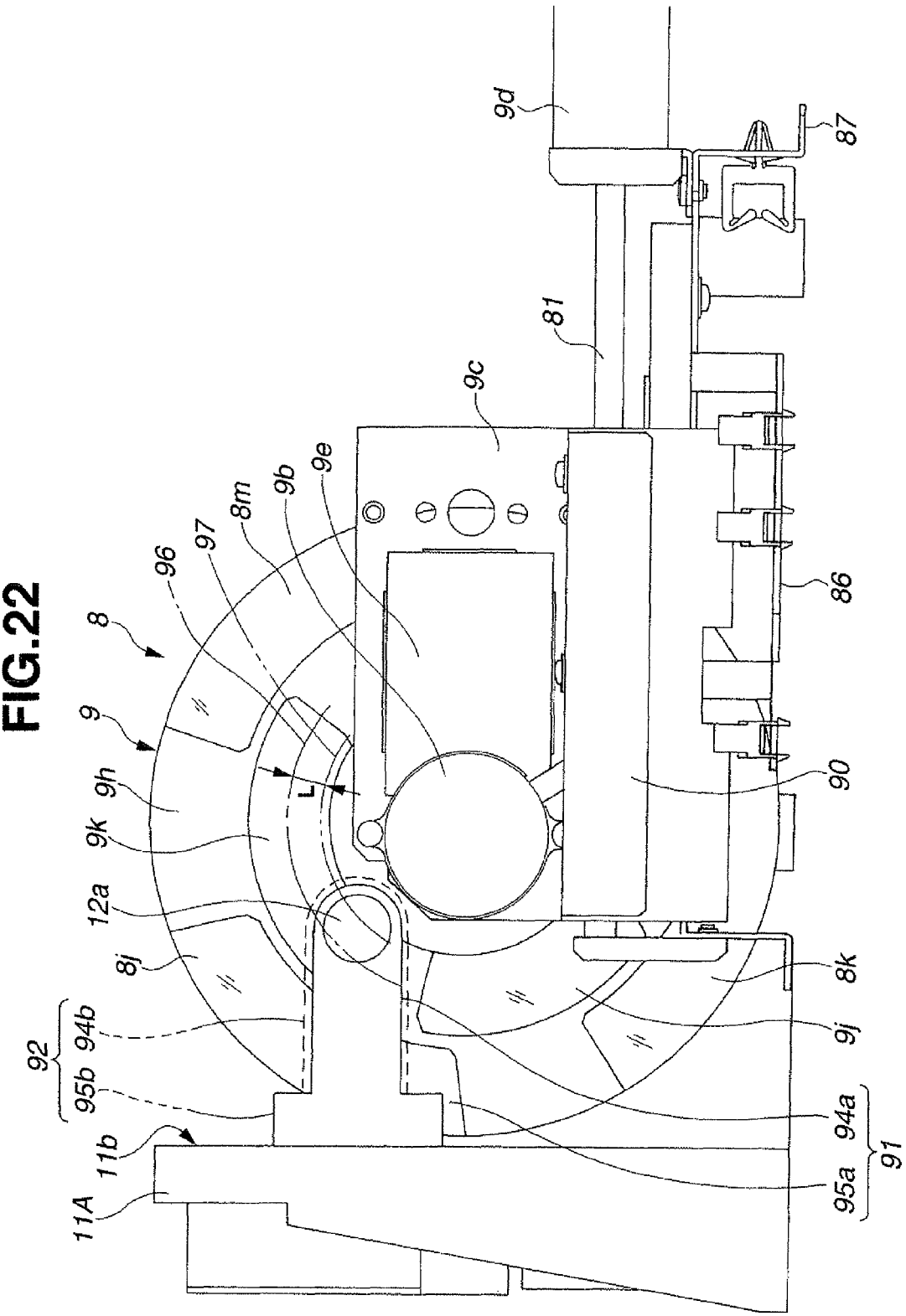
FIG. 22 is a view that illustrates the relation between a light-condensing device comprising a lens holding member and the lens holder shown in FIG. 21, and the third rotary filter unit and the fourth rotary filter unit.

The relation between the light-condensing device 10A comprising the lens holder 11A, and the third rotary filter unit 8 and fourth rotary filter unit 9 will now be described referring to FIG. 22.

In the light source device 2 of the present embodiment, the lenses 12a, 12b, 12c, and 12d are mounted in the lens disposing portions 94a, 94b, and 94c of the lens holding members 91, 92, and 93 corresponding to the respective lenses. The lens holding members 91, 92, and 93 protrude in a predetermined direction from the one side face 11b. Therefore, as shown in FIG. 22, for example, when the second base plate 9c is moved in the direction of the lens holder 11A to bring the motor 9b adjacent to the lens disposing portion 94a of the lens holding member 91, the optical axis of the lens 12a can be moved to the position of a center line 97 that is closer to a center hole 9f by a distance L from a center line 96 of the opening portion 9g provided in the fourth rotary plate 9a.

As a result, it is possible to decrease the size of the lens holder 11A and further shorten the distance from the center of the fourth rotary plate 9a to the center of the lens.

Thus, a lens is mounted in a lens holding member, the lens holding member is fixedly arranged on one side face of a lens holder, and the lens that is mounted in the lens disposing portion is allowed to protrude. It is thereby possible to bring the rotary motor more closer to the lens, further shorten the distance from the center of the rotary plate to the center of the lens, and decrease the diameter of a rotary plate or provide multiple filters in a rotary plate.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A light source device comprising:
a light source lamp for emitting illumination light;
a light-condensing device including:
a lens holder,
a lens protruding from a predetermined side face of the lens holder, for condensing illumination light emitted from the light source lamp, and
at least one lens holding member fixed to the predetermined side face of the lens holder for holding the lens such that an optical axis of the lens aligns with an optical axis of the illumination light; and
a rotary filter unit comprising:
a rotary plate provided with a plurality of optical filters to be placed in the optical path of the illumination light,
a rotary driving portion that rotates the rotary plate, and a forward and rearward driving portion that is capable of moving the rotary plate forward and rearward in a direction perpendicular to the illumination light path,
wherein the lens holder of the light-condensing device is provided with a hole in the predetermined side face, which defines a rotary plate disposing space portion in which the rotary plate is removably disposed when said plate is moved by the forward and rearward driving portion along the direction perpendicular to the illumination light path.

2. The light source device according to claim 1, wherein a protrusion amount of the lens from the predetermined side face of the lens holder is set to a predetermined dimension, and in a state in which one of the optical filters of the rotary plate is disposed in the illumination light path, the rotary driving portion is disposed adjacent to the lens holding member without interfering therewith.

3. The light source device according to claim 2, wherein the rotary plate disposing space portion is configured by a clearance between two of the at least one lens holding members protruding from the predetermined side face of the lens holder.

4. The light source device according to claim 1, wherein the lens holder comprises:
an optical path formation groove formed in a straight line shape, having an opening on the predetermined side face side of the lens holder, having a trapezoidal cross-sectional shape, and serving as an illumination light path; and
at least one lens disposition concave portion in which the lens fixed on the predetermined side face by the lens holding member is disposed, the lens disposition concave portion having a shape corresponding to a width dimension and thickness dimension of the lens, so that the lens is exposed from the opening of the optical path formation groove.

5. The light source device according to claim 1, wherein the lens holder comprises an aperture disposing space portion formed therein.

* * * * *